(12) United States Patent
Cardelino et al.

(10) Patent No.: US 12,369,843 B2
(45) Date of Patent: Jul. 29, 2025

(54) METHODS AND SYSTEMS FOR ANALYZING SKIN AND PROVIDING INFORMATION VIA A GRAPHICAL USER INTERFACE (GUI)

(71) Applicant: Ulta Salon, Cosmetics & Fragrance, Inc., Bolingbrook, IL (US)

(72) Inventors: Juan Cardelino, Bolingbook, IL (US); Agustina Sartori, Bolingbrook, IL (US); Andrew McGarry, Bolingbrook, IL (US); Javier Camacho, Bolingbrook, IL (US); Faris Alqadah, Bolingbrook, IL (US)

(73) Assignee: Ulta Salon, Cosmetics & Fragrance, Inc., Bolingbrook, IL (US)

( * ) Notice: Subject to any disclaimer, the term of this patent is extended or adjusted under 35 U.S.C. 154(b) by 881 days.

(21) Appl. No.: 17/475,194

(22) Filed: Sep. 14, 2021

(65) Prior Publication Data
US 2023/0077452 A1  Mar. 16, 2023

(51) Int. Cl.
*A61B 5/00* (2006.01)
*G16H 20/00* (2018.01)
(Continued)

(52) U.S. Cl.
CPC .......... *A61B 5/442* (2013.01); *A61B 5/7267* (2013.01); *A61B 5/7475* (2013.01); *G16H 20/00* (2018.01);
(Continued)

(58) Field of Classification Search
CPC ......... G06T 11/00; G06T 7/0016; G06T 7/90; G06T 2200/24; G06T 2207/10024; G06T 2207/30088; G06T 7/0012; G06T 2207/20081; G06T 2207/20084; G06T 2207/30201; G06T 19/006; G06T 19/20; G06T 2219/2012; A61B 5/004; A61B 5/441; A61B 5/742; A61B 5/7475; A61B 2576/02; A61B 5/444; A61B 5/1032; A61B 5/1034; A61B 5/411; A61B 5/442;
(Continued)

(56) References Cited

U.S. PATENT DOCUMENTS 6,571,003 B1   5/2003   Hillebrand et al.
7,437,344 B2  10/2008   Peyrelevade
(Continued)

*Primary Examiner* — Jennifer Robertson
*Assistant Examiner* — Elina Sohyun Jang
(74) *Attorney, Agent, or Firm* — McDonnell Boehnen Hulbert & Berghoff LLP

(57) ABSTRACT

An example computer-implemented method for analyzing skin of a user comprises requesting, via a graphical user interface (GUI), visual media including a face of the user, processing the visual media to generate information for each of a plurality of skin conditions of the face of the user and the information comprises a score per each of a plurality of zones of the face of the user per each of the plurality of skin conditions of the face of the user, mapping the score to a severity level associated with the plurality of skin conditions, and for each of the plurality of skin conditions, the GUI overlaying computer graphics at locations onto the visual media corresponding to the plurality of zones of the face of the user. The computer graphics are depicted with a color associated with the severity level for the skin condition at each of the locations.

20 Claims, 18 Drawing Sheets

(51) Int. Cl.
*G16H 50/20* (2018.01)
*G16H 50/30* (2018.01)
*G16H 50/70* (2018.01)

(52) U.S. Cl.
CPC .............. *G16H 50/20* (2018.01); *G16H 50/30* (2018.01); *G16H 50/70* (2018.01)

(58) Field of Classification Search
CPC ....... A61B 5/445; A61B 5/446; A61B 5/7264; A61B 5/0088; A61B 5/7267; A61B 5/0013; A61B 5/0022; A61B 5/6897; A61B 5/443; A61B 5/0077; A61B 5/0095; A61B 5/746; A61B 5/6898; A61B 5/7405; A61B 5/0064; G16H 30/20; G16H 30/40; G16H 50/50; G16H 10/60; G16H 10/20; G16H 20/00; G16H 40/67; G16H 50/20; G16H 50/30; G16H 50/70; G16H 70/20; G16H 20/10; G16H 20/60; G06F 17/18; G06F 3/011; G06F 3/0488; G06F 16/436; A45D 44/005; A45D 2044/007; G06Q 30/0601; G06Q 30/0631; G06Q 30/0621; G06Q 30/0633; G06Q 30/01; G06Q 30/0641; G06Q 30/0643; G06Q 30/0261; G06Q 30/0271; G06Q 30/0623; G16Z 99/00; H04N 23/661; G06N 3/045; G06N 3/08; G06N 5/01; G06N 7/01; G06N 20/10; G06V 10/454; G06V 10/82; G06V 40/171; G06V 40/174; G06V 40/18; G06V 2201/03; G06V 10/26; G06V 10/56; G06V 10/764; G06V 10/774; G06V 10/776; G06V 40/10; G06V 20/20; G06V 40/165; G06V 40/169; G06V 2201/10; G06V 20/64; G06V 40/161; G06V 20/60; H04L 51/10; H04L 51/18

See application file for complete search history.

(56) References Cited

U.S. PATENT DOCUMENTS

| | | | |
|---|---|---|---|
| 7,584,159 | B1 | 9/2009 | Chakrabarti et al. |
| 7,634,103 | B2 | 12/2009 | Rubinstenn et al. |
| 8,094,186 | B2 | 1/2012 | Fukuoka et al. |
| 8,386,406 | B2 | 2/2013 | Bolivar et al. |
| 8,756,186 | B2 | 6/2014 | Bolivar et al. |
| 9,525,867 | B2 | 12/2016 | Thomas et al. |
| 10,255,482 | B2 | 4/2019 | Morgana et al. |
| 10,713,704 | B2 | 7/2020 | Aarabi |
| 10,990,858 | B2 | 4/2021 | Ludwinski et al. |
| 11,010,636 | B2 | 5/2021 | Charraud et al. |
| D923,043 | S | 6/2021 | Miyamoto et al. |
| 2009/0228298 | A1* | 9/2009 | Xue ................... A61B 5/349 705/2 |
| 2018/0352150 | A1* | 12/2018 | Purwar ................... G06T 7/536 |
| 2019/0244274 | A1 | 8/2019 | Chang et al. |
| 2020/0170564 | A1* | 6/2020 | Jiang .................. A61B 5/0077 |
| 2020/0265937 | A1 | 8/2020 | Anyanwu-Ofili et al. |
| 2020/0384229 | A1* | 12/2020 | Lashinsky ............ G16H 50/50 |
| 2021/0015240 | A1 | 1/2021 | Elfakhri et al. |
| 2022/0020077 | A1* | 1/2022 | Lindgren ............ G06V 40/171 |
| 2022/0344044 | A1* | 10/2022 | Yoo .................... G16H 50/20 |

* cited by examiner

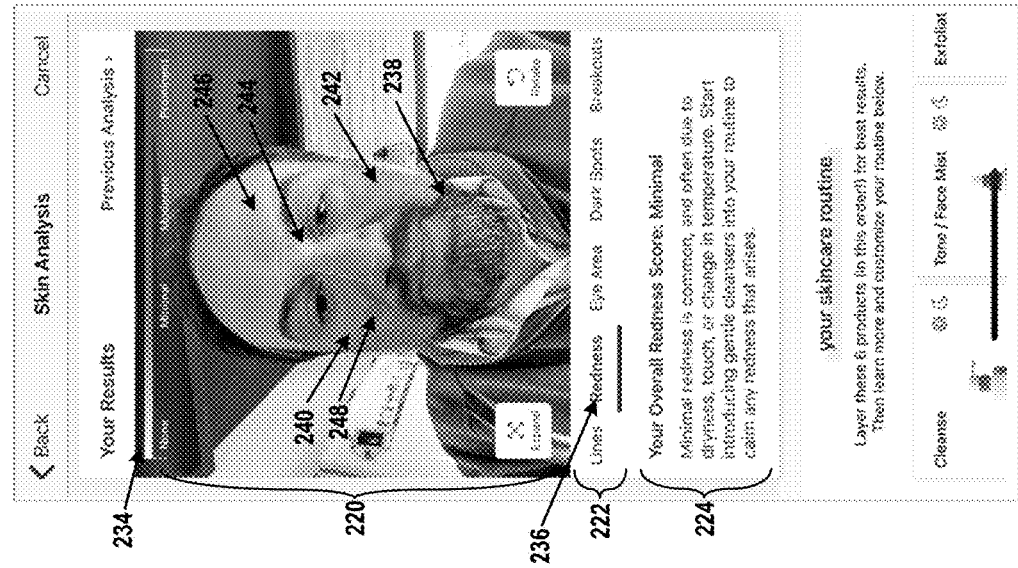 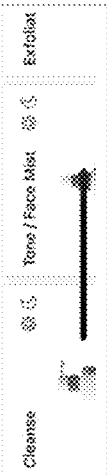
FIG. 19
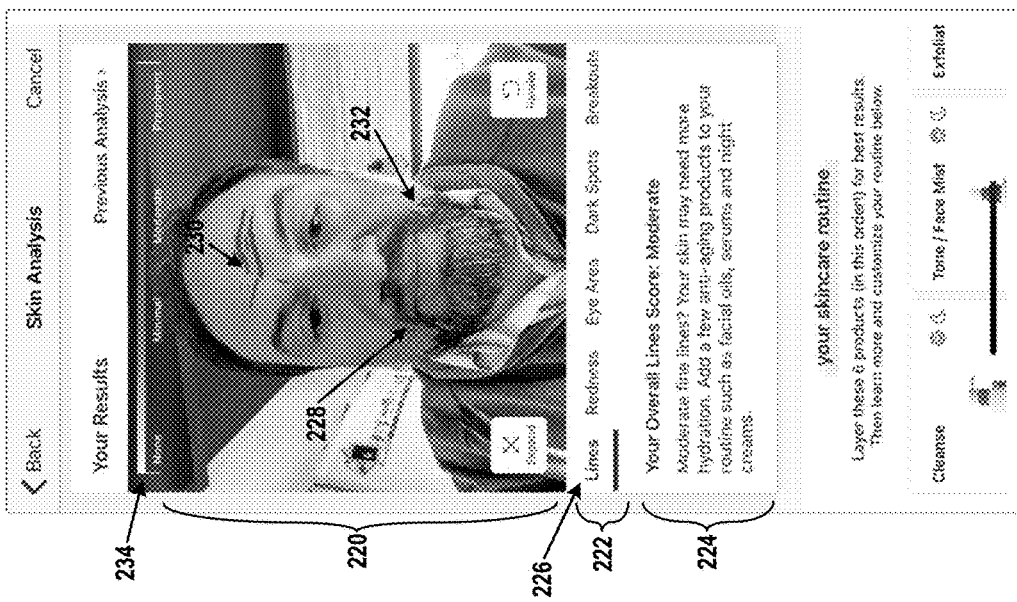 
FIG. 18

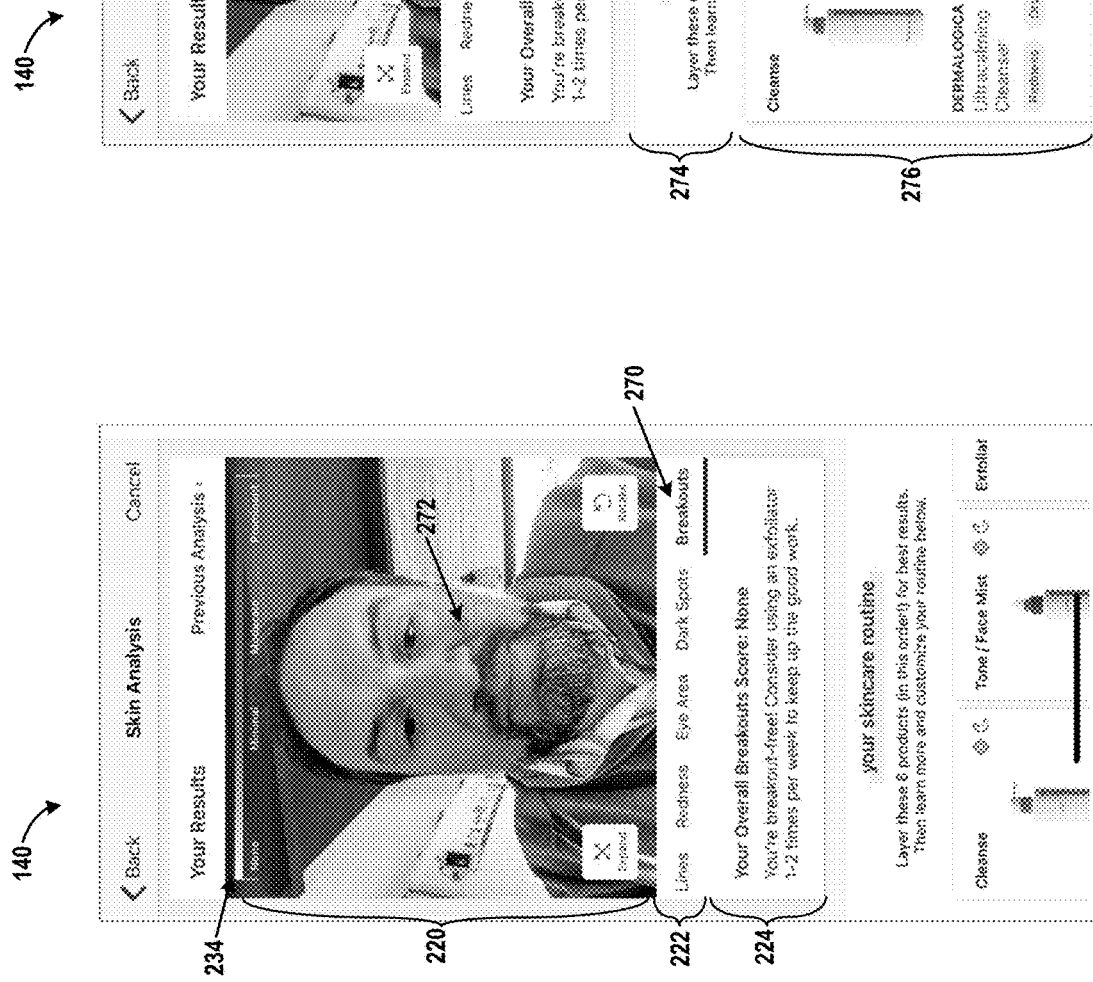

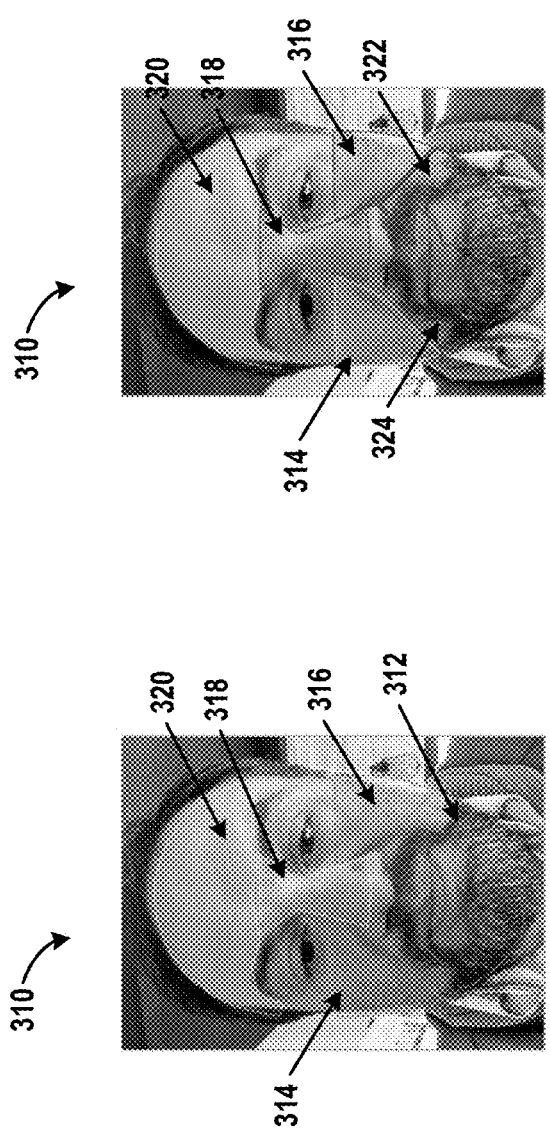
FIG. 28
FIG. 29
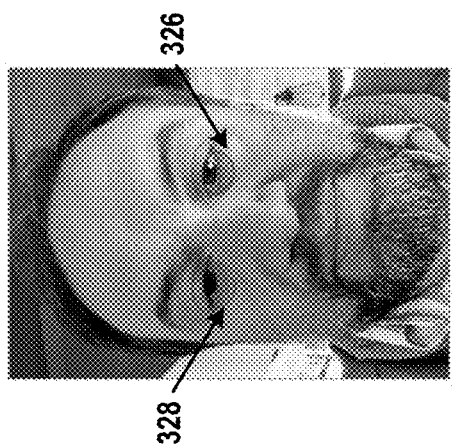
FIG. 30

METHODS AND SYSTEMS FOR ANALYZING SKIN AND PROVIDING INFORMATION VIA A GRAPHICAL USER INTERFACE (GUI)

FIELD

The present disclosure relates generally to methods and systems for analyzing skin and providing information via a Graphical User Interface (GUI), and more particularly to, generating and overlaying computer graphics at locations onto visual media including a face of a user corresponding to zones of the face of the user and the computer graphics are depicted with a color associated with the severity level for a skin condition at each of the locations of the face of the user.

BACKGROUND

Each person has skin with unique characteristics, and each person has unique objectives for skin treatment. Often times, identifying an existing skin condition that is present can be difficult for a person.

Furthermore, with the numerous skin-care brands and products available, it can be difficult to identify which products are helpful to achieve the objectives of the person as well as offer appropriate skin care treatment, as needed.

SUMMARY

Within examples, a computer-implemented tool is described that uses machine learning, in some aspects, to analyze skin and help discover products with active ingredients that are customized to preferences and goals of a user as well as for active treatment of skin of the user for improvement of a specified skin condition.

In one example, a computer-implemented method for analyzing skin of a user is described. The method comprises requesting, via a graphical user interface (GUI), visual media including a face of the user, processing the visual media to generate information for each of a plurality of skin conditions of the face of the user and the information comprises a score per each of a plurality of zones of the face of the user per each of the plurality of skin conditions of the face of the user, mapping the score per each of the plurality of zones of the face of the user and for each of the plurality of skin conditions of the face of the user to a severity level associated with the plurality of skin conditions, and for each of the plurality of skin conditions, the GUI overlaying computer graphics at locations onto the visual media including the face of the user corresponding to each zone of the plurality of zones of the face of the user. The computer graphics are depicted with a color associated with the severity level for the skin condition at each of the locations of the face of the user.

In another example, a system for analyzing skin of a user is described. The system comprises a computing device comprising one or more processors and non-transitory computer-readable media having stored therein executable instructions, which when executed by the one or more processors, causes the computing device to perform functions. The functions comprise requesting, via a graphical user interface (GUI), visual media including a face of the user, processing the visual media to generate information for each of a plurality of skin conditions of the face of the user and the information comprises a score per each of a plurality of zones of the face of the user per each of the plurality of skin conditions of the face of the user, mapping the score per each of the plurality of zones of the face of the user and for each of the plurality of skin conditions of the face of the user to a severity level associated with the plurality of skin conditions, and for each of the plurality of skin conditions, the GUI overlaying computer graphics at locations onto the visual media including the face of the user corresponding to each zone of the plurality of zones of the face of the user. The computer graphics are depicted with a color associated with the severity level for the skin condition at each of the locations of the face of the user.

In another example, a non-transitory computer-readable media having stored therein executable instructions, which when executed by a computing device having one or more processors causes the computing device to perform functions. The functions comprise requesting, via a graphical user interface (GUI), visual media including a face of the user, processing the visual media to generate information for each of a plurality of skin conditions of the face of the user and the information comprises a score per each of a plurality of zones of the face of the user per each of the plurality of skin conditions of the face of the user, mapping the score per each of the plurality of zones of the face of the user and for each of the plurality of skin conditions of the face of the user to a severity level associated with the plurality of skin conditions, and for each of the plurality of skin conditions, the GUI overlaying computer graphics at locations onto the visual media including the face of the user corresponding to each zone of the plurality of zones of the face of the user. The computer graphics are depicted with a color associated with the severity level for the skin condition at each of the locations of the face of the user.

The features, functions, and advantages that have been discussed can be achieved independently in various examples or may be combined in yet other examples. Further details of the examples can be seen with reference to the following description and drawings.

BRIEF DESCRIPTION OF THE FIGURES

Examples, objectives and descriptions of the present disclosure will be readily understood by reference to the following detailed description of illustrative examples when read in conjunction with the accompanying drawings, wherein:

FIG. 12 is a screen capture of an example of the GUI illustrating skin analysis questions for recommendations, according to an example implementation.

FIG. 13 is a screen capture of an example of the GUI illustrating skin analysis questions for recommendations, according to an example implementation.

FIG. 18 is a screen capture of an example of skin analysis results displayed by the GUI for lines, according to an example implementation.

FIG. 19 is a screen capture of an example of skin analysis results displayed by the GUI for redness, according to an example implementation.

FIG. 22 is a screen capture of an example of skin analysis results displayed by the GUI for breakouts, according to an example implementation.

FIG. 23 is a screen capture of an example of skin analysis results displayed by the GUI for recommendations, according to an example implementation.

FIG. 28 is a conceptual illustration of an image of a face of a user divided into zones, according to an example implementation.

FIG. 29 is another conceptual illustration of the image of the face of the user divided into different zones, according to an example implementation.

FIG. 30 is another conceptual illustration of the image of the face with further zones identified, according to an example implementation.

DETAILED DESCRIPTION

Figure 1:
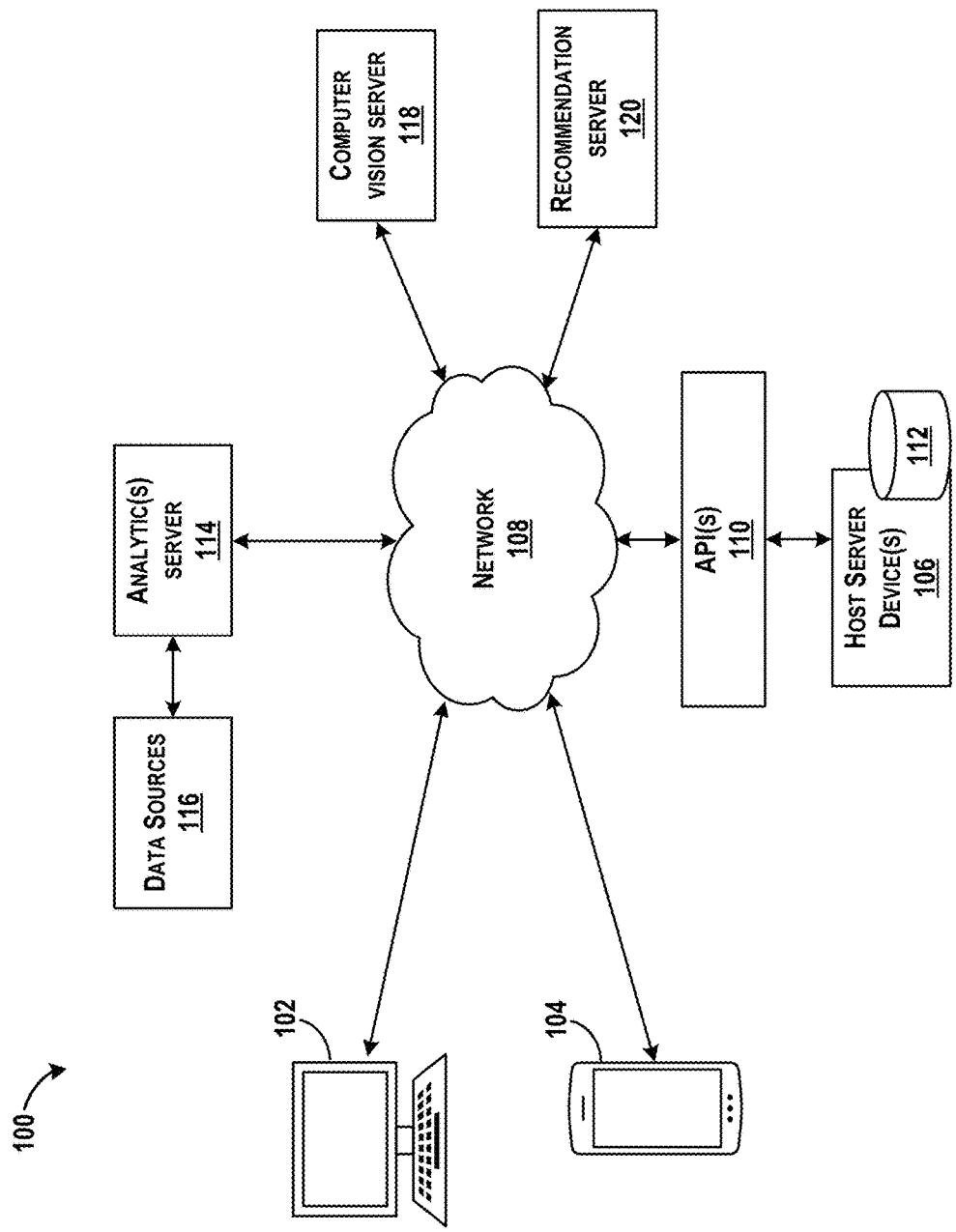
FIG. 1 is a block diagram illustrating an example of a networked computer system, according to an example implementation.

Disclosed examples will now be described more fully hereinafter with reference to the accompanying drawings. Several different examples are described and should not be construed as limited to all possible alternatives. Rather, these examples are described so that this disclosure is thorough and complete and fully conveys a scope of the disclosure to those skilled in the art.

Within examples, systems and methods described herein are beneficial to perform a metric based analysis of skin of the user, and provide a GUI for display of a graphical representation easily understood by the user of a number of possible skin conditions that have been identified. The GUI further displays graphical indicators at locations where the skin conditions are present on the face of the user with information indicating a severity level of the skin condition.

The systems and methods described herein also provide a solution to help identify skin care products, routines, and/or services beneficial to a user to (i) achieve identified goals (ii) within preferences of the user that (iii) provide active or clinical treatment of the skin. Thus, implementations of this disclosure provide technological improvements that are particular to computer technology, for example, those concerning computer vision, computer graphical representation, and product data analysis. Computer-specific technological problems, such as analyzing a digital image for determination of a skin condition, can be wholly or partially solved by implementations of this disclosure. For example, implementation of this disclosure allows for many types of media (including both visual and non-visual) that is indicative of or includes a face of a user to be analyzed and annotated per zone of a face of a user to identify a skin condition of each zone. The analysis further includes a mapping to a severity level, on a zone-by-zone basis, of each identified skin condition. Once the mapping is performed, machine learning systems are utilized to identify recommended products, services, routines, tutorials, and other information for user and implementation by the user.

Implementations of this disclosure thus introduce new and efficient improvements in the ways in which products, services, and routines are offered or recommended to users that take into account skin conditions, as well as, (i) product data, (ii) user product preferences, (iii) user concerns and goals, and (iv) past user behavior (e.g., purchases). The skin conditions are based on objective measurements performed on visual media (e.g., digital image) of the face of the user, and consider intrinsic visual characteristics including facial features that characterize the user, such as color measurements (i.e., skin tone), geometric measurements (i.e., eye shape/position, face shape, etc.), and dermatological conditions (such as redness, wrinkles, etc.) that can be temporary, non-permanent, seasonal, or reoccurring, for example.

Product data includes details concerning identified clinical treatment data of the product (e.g., based on testing of the product), ingredients used in the elaboration of the product and conscious beauty data (which includes labels related to vegan, cruelty free, environment friendly, etc.).

User product preferences include specific details or ingredients of products for which the user prefer to use or not use (i.e., prefers vegan products) and preferred brands.

User concerns and goals includes a manifestation of interests and needs of the user. For example, goals include interests of the user with respect to their skin progression (e.g., improving hydration of the skin), and concerns are conditions that preoccupy the user (e.g., a localized irritation/inflammation manifested as redness).

The implementations of the present disclosure thus introduce new and efficient improvements in the ways recommendations are generated and offered to users in a graphical manner. The recommendations represent any type of product, entity, or service that is offered to a user based on the combination of the goals, skin conditions, and characteristics, along with any commercial sale data for products (e.g., promotions, trends, best sellers, etc.). Recommendations can include products to be bought, routines to be followed to take care of skin (e.g., applying different products at different times of the day, changing diet, modify water drinking habits, etc.), and services to consider (e.g., appoint a session with a skin expert according to needs and detected conditions.

The systems and methods of the present disclosure further address problems particular to computer networks, for example, those concerning processing of visual media including a face of a user and privacy of the user. These computing network-specific issues can be solved by implementations of the present disclosure. For example, in an instance where a user consents to use of the visual media including the face of the user, such data may be used for performing analysis of the skin through machine learning algorithms. In any situations in which systems described herein collect personal information about users, or process information to generate personal information of user, the users may be provided with opportunities to control whether the systems proceed to collect the user information. In addition, some user data may be processed before stored or used so that personally identifiable information is removed. Furthermore, in some examples, a user has further capabilities to request for deletion of user data at any time.

FIG. 1 is a block diagram illustrating an example of a networked computer system 100, according to an example implementation. The networked computer system 100 includes one or more client devices 102 and 104 coupled to one or more host server device(s) 106 via a network 108. The network 108 represents one or more local area networks (LANs), wide area networks (WANs), cellular networks, and/or other networks using any of wired, wireless, terrestrial microwave, or satellite links, and may include the public Internet.

The client devices 102 and 104 can be a special purpose data processor, a general-purpose computer, smartphone, tablet, a computer system, or a group of networked computers or computer systems configured to perform steps or modes of methods described herein. Further examples of the client devices 102 and 104 may include, without limitation, handheld computers, wearable devices, laptop computers, desktop computers, servers, portable media players, gaming devices, in-store kiosks, and so forth. According to one example, the client devices 102 and 104 are built on a personal computer platform, such as the Apple® or Android® platform. Although FIG. 1 illustrates two of the client devices 102 and 104, the networked computer system may include fewer or more of the client devices 102 and 104 operating at any time.

The host server devices(s) 106 may include any number of computers, virtual machine instances, and/or data centers that are configured to host or execute one or more instances of host applications. The host server devices(s) 106 may be involved, directly or indirectly, in processing requests received from the client devices 102 and 104. The host server devices(s) 106 may comprise, for example, one or more of a network device, a web server, an application server, a database server, etc. A collection of the host server devices(s) 106 may be configured to implement a network-based service. For example, a provider of a network-based service may configure one or more of the host server devices(s) 106 and host applications (e.g., one or more web servers, application servers, database servers, etc.) to collectively implement a network-based application.

The client devices 102 and 104 communicate with one or more host applications at the host server devices(s) 106 to exchange information. The communication between the client devices 102 and 104 and a host application may, for example, be based on the Hypertext Transfer Protocol (HTTP) or any other network protocol. Content delivered from the host application to the client devices 102 and 104 may include, for example, HTML documents, media content, etc. The communication between the client devices 102 and 104 and a host application may include sending various requests and receiving data packets. For example, the client devices 102 and 104 or an application running on the client devices 102 and 104 may initiate communication with a host application by making a request for a specific resource (e.g., based on an HTTP request), and the host server devices(s) 106 may respond with the requested content stored in one or more response packets.

Thus, one or more client applications may be executed at the client devices 102 and 104. Some applications executing at the client devices 102 and 104 may implement one or more application programming interfaces (APIs) 110. The APIs 110, for example, process inputs and control outputs of the client devices 102 and 104. For example, a client application executing at the client devices 102 and 104 accesses the host server device(s) 106 via the API 110 to retrieve configuration parameters for a particular requested skin advisor platform. The client application then uses local image processing libraries along with retrieved configuration parameters to generate visual media in response to a request by the host server device(s) 106.

The APIs 110 serve as an interface between the client devices 102 and 104 and the host server device(s) 106. One or more repositories and/or databases 112, which support certain utilities, may store content required for implementing the skin advisor platform described herein, and is accessible by the host server device(s) 106. For example, the databases 112 store host applications, content (e.g., images/video), data related to image processing (e.g., image processing libraries, computer graphics, predefined visual effects, etc.), information relevant to the users (e.g., registration information or usage statistics), metadata, and any other data used in implementing the techniques described herein.

Thus, in some examples, techniques described herein are provided by a skin advisory platform that is made accessible via a website or an application via the API 110. Alternatively, or in addition, techniques described herein are offered as a platform product directly implementable on various devices or systems.

The networked computer system 100 also includes an analytic(s) server 114. The analytic(s) server 114 performs analytics on data related to usage behavior of the networked computer system 100. Such analytics may support other services including product recommendations and targeted marketing.

The networked computer system 100 also includes one or more data sources 116 accessible by the analytic(s) server 114. The data sources 116 generally refer to any sources from which data is received to implement features described herein. As a few illustrative examples, the data sources 116 include makeup product vendors, manufacturers, retailers, etc., content providers/licensing services, modeling services, and machine generated data sources such as server log files, activity log files, configuration files, messages, network packet data, performance measurements, sensor measurements, and the like.

The networked computer system 100 also includes a computer vision server 118. The computer vision server 118 is in communication with the client devices 102 and 104 and the host server device(s) 106 via the network 108 to receive visual media including a face, a body, or a portion of a face or body of a user, and process the visual media to generate information for a number of different skin conditions detected. The visual media can include a digital image, multiple frames of images, video, etc., and the images can include visible images (red, green, blue color images), infrared images.

The computer vision server 118 includes computational ability to perform computer vision tasks for identifying and localizing a face in an image (e.g., using any number of algorithms such as the classical feature-based cascade classifier using the OpenCV library or a Multi-task Cascade convolutional neural network (MTCNN) via the MTCNN library) to find coordinates of the face in the image or demarcating an extent of the face (e.g., with a bounding box). Following, the computer vision server 118 identifies landmarks on the face (e.g., nose, eyes, lips, etc.) through any number of algorithms or through use of pre-trained models in a machine learning algorithm. The computer vision server 118 then outputs, to the host server device(s) 106 and/or to the client devices 102 and 104, information for each of a plurality of skin conditions of the face of the user as a score per each of a plurality of zones of the face of the user. The zones are predefined areas of the face characterized based on the identified landmarks. Example zones include a forehead area, a cheek area, a chin area, an eye area, a nose area, etc.

A skin condition describes an extrinsic dermatological affection that manifests itself visually on a surface of the skin of the user. As will be described more fully below, a skin condition may include wrinkles, redness, dullness, discoloration, acne or breakouts, oiliness, puffiness, dark circles, etc.

The networked computer system 100 also includes a recommendation server 120. The recommendation server 120 can include or have access to a database containing product information, beauty services information, etc., which is accessible via the network 108 by the host server device(s) 106. The host server device(s) 106 then uses information from the output of the computer vision server 118 to select or receive an applicable product, entity, or service from the recommendation server 120 that would address an identified skin condition of the user detected in the visual media.

Figure 2:
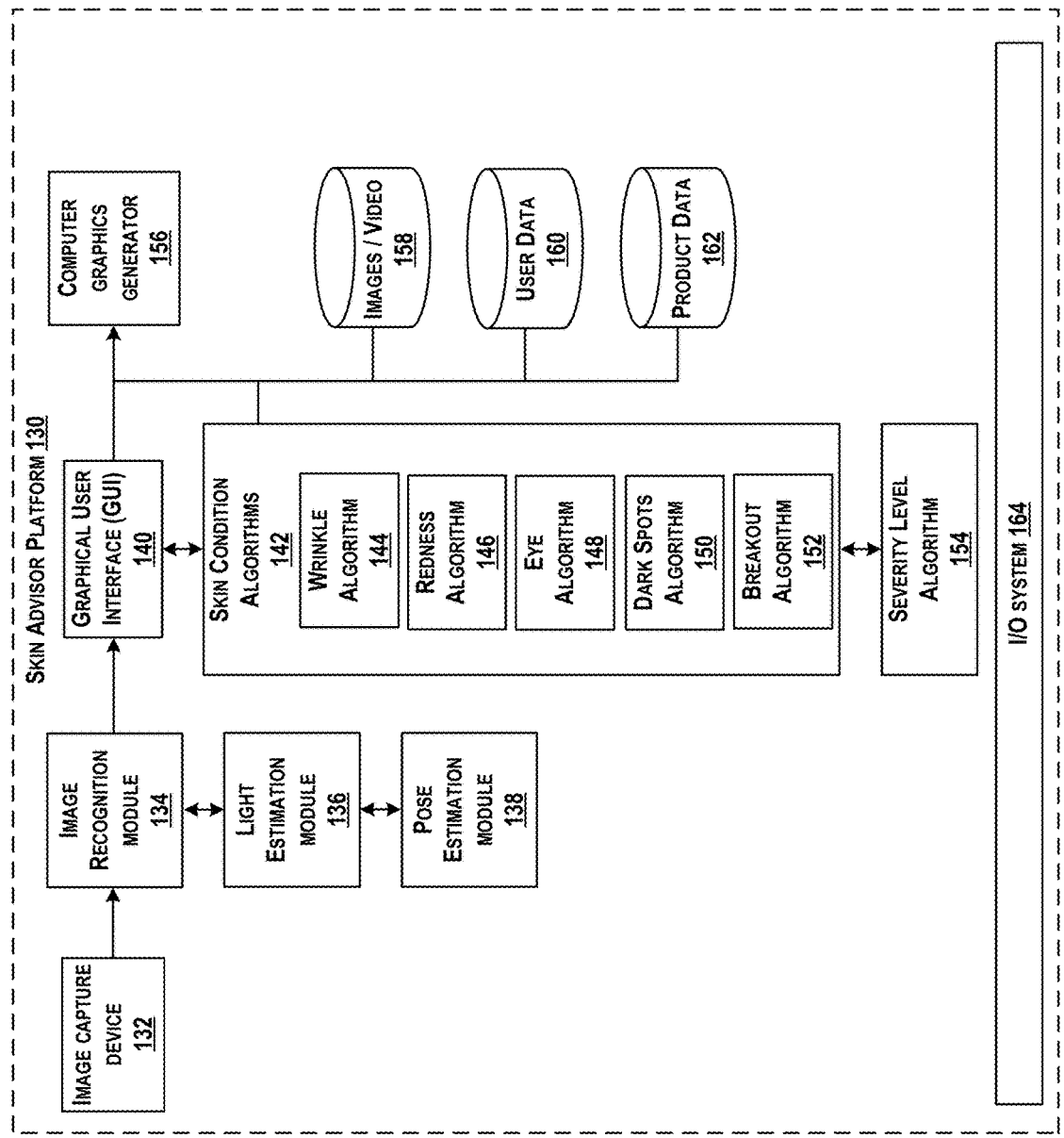
FIG. 2 illustrates a block diagram of a skin advisor platform, according to an example implementation.

FIG. 2 illustrates a block diagram of a skin advisor platform 130, according to an example implementation. Within examples, some or all of the components of the networked computer system 100 perform some functions of the skin advisor platform 130. Depending upon a particular implementation, the various components described with respect to FIG. 2 are implemented at a single computing device (e.g., the host server device(s) 106 or one of the client devices 102 and 104) or distributed across several computing devices or servers. In some examples, certain functionalities of the skin advisor platform 130 (e.g., image capture) are performed at one of the client devices 102 and 104 while other functionalities (e.g., image recognition) are performed at a remote server device, such as the computer vision server 118.

Figure 3:
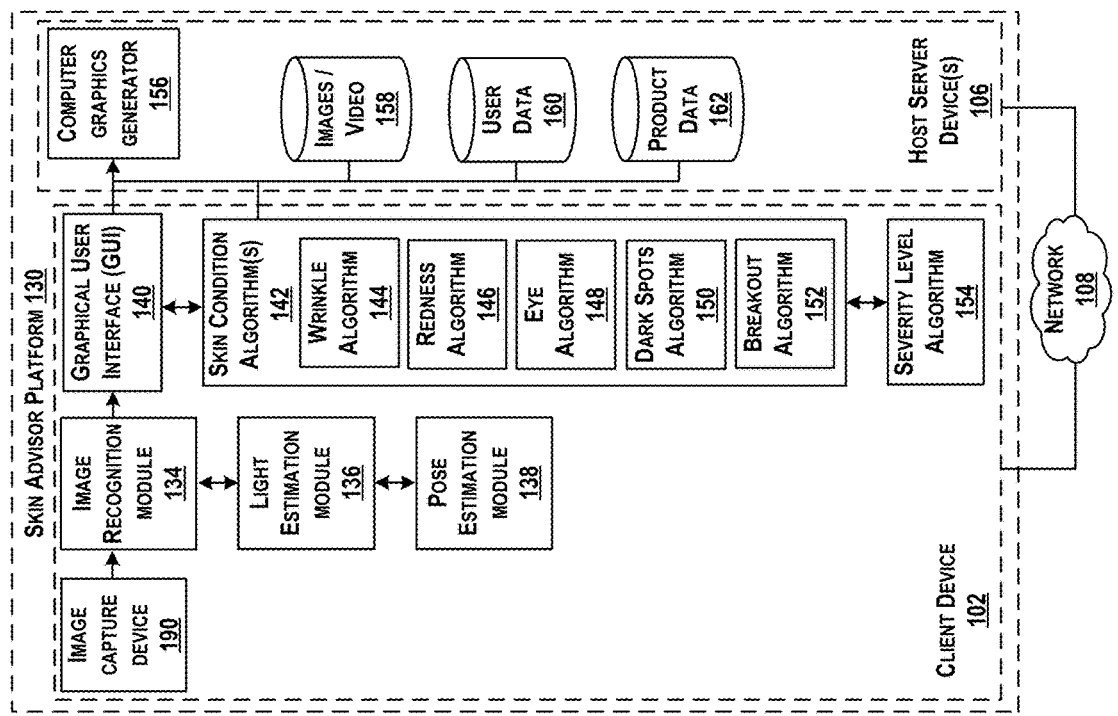
FIG. 3 illustrates a block diagram of an example implementation of the skin advisor platform, according to an example implementation.

FIG. 3 illustrates a block diagram of an example implementation of the skin advisor platform 130, according to an example implementation, in which some components described with respect to FIG. 2 are instantiated at the client devices 102 and some components are instantiated at the host server device(s) 106, and in which the client device 102 and the host server device(s) are communicatively coupled via the network 108.

Figure 4:
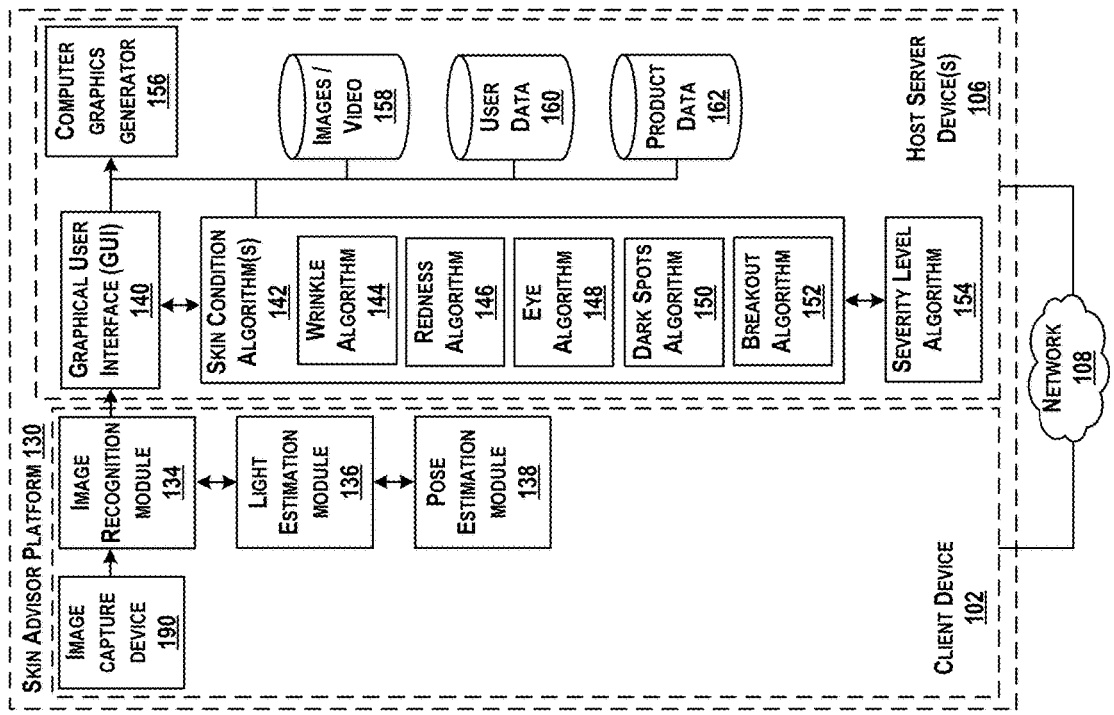
FIG. 4 illustrates a block diagram of another example implementation of the skin advisor platform, according to an example implementation.

FIG. 4 illustrates a block diagram of another example implementation of the skin advisor platform 130, according to an example implementation, in which other components described with respect to FIG. 2 are instantiated at the client devices 102 and other components are instantiated at the host server device(s) 106, and in which the client device 102 and the host server device(s) are communicatively coupled via the network 108.

The example implementations shown in FIGS. 3 and 4 are provided for illustrative purposes only, and components of the skin advisor platform 130 are be distributed differently in other examples.

With reference to FIGS. 2-4, some components are described as "modules" or "engines", and such components include general purpose or special purpose hardware (e.g., general or special purpose processors), firmware, an/or software embodied in a non-transitory computer-readable (storage) medium for execution by one or more processor to perform described functionality.

The skin advisor platform 130 includes an image capture device 132 in a form of software and/or hardware for capturing media (images or video) at one of the client devices 102 and 104. For example, the image capture device 132 includes a digital camera including one or more optical sensors for conversion of received light to visual media such as digital information (e.g., charge-coupled devices (CCD), complementary metal-oxide semiconductor (CMOS) phototransistors, etc.). In another example, the image capture device 132 also includes software for pre-processing raw image data.

Within examples, the skin advisor platform 130 enables capture of many different kinds of media that includes or is indicative of the face of the user. One type includes visual media, such as a single digital image, multiple digital images, and videos. Other types include non-visual media, such as infrared (IR) images or data, and hyperspectral images or data. Still other types of media include media captured based on the visible light spectrum or other spectral bands such as ultra-violet (UV). A number of media captured and a type of media captured depends on image capture sensors or devices available or included on the client devices 102 and 104. In examples where non-visual media is captured, such data is useful for further analysis of the face to determine contours and other three-dimensional (3D) aspects.

An image recognition module 134 receives or retrieves the visual media of a face of the user from the image capture device 132, and processes the visual media to: first, determine if a face is present or not, second, detect the bounding box of the face, third perform detection of the facial features, and finally assist with generation of information for each of a plurality of skin conditions of the face of the user in a form of a score per each of a plurality of zones of the face of the user. The processing results in generation of information for one or more of discoloration, wrinkles, lines, dark spots, redness, dullness, oiliness, puffiness, and breakouts on the face of the user per each of a nose area, a chin area, a cheek area, and a forehead area on the face of the user.

The skin advisor platform 130 further includes a light estimation module 136 to evaluate one or more characteristics of illumination for the visual media. Based on the one or more characteristics of illumination for the visual media not meeting a quality level, the light estimation module 136 requests a new visual media including the face of the user with an adjustment to lighting in an environment of the user.

The skin advisor platform 130 further includes a pose estimation module 138 to evaluate one or more characteristics of a pose of the face of the user in the visual media. Based on the one or more characteristics of the pose of the face of the user in the visual media indicating a threshold amount of the face of the user is not included in the visual media, the pose estimation module 138 requests the user to adjust a position of the face for capture of new visual media.

The skin advisor platform 130 further includes a graphical user interface (GUI) 140 that allows users to interact with the client devices 102 and 104 through graphical icons and audio indicators, typed command labels or text navigation. The GUI 140 includes interactive elements selectable for providing input by a user or receiving outputs by the GUI 140. The GUI 140 operates to provide information based on skin condition algorithms 142 executable to identify and/or determine one of a plurality of skin conditions of the face of the user in a form of a score per each of a plurality of zones of the face of the user. The skin condition algorithms 142 include a wrinkle algorithm 144, a redness algorithm 146, an eye algorithm 148, a dark spots algorithm 150, and a breakout algorithm 152. More or fewer skin condition algorithms 142 may be included as well. Details of each of the skin condition algorithms 142 are discussed more fully below.

The GUI 140 further provides information to the user based on outputs of a severity level algorithm 154, which is executable to map the score per each of the plurality of zones of the face of the user and for each of the plurality of skin conditions of the face of the user to a severity level associated with the plurality of skin conditions. Within examples, the severity level is based on a continuous level from zero to maximum amount, or is based on discrete levels such as none, minimal, moderate, prominent, etc.

The skin advisor platform 130 further includes a computer graphics generator 156 to generate or select computer graphics applicable for display by the GUI 140 to be representative of identified skin conditions and associated with the identified severity level. For example, for each of the plurality of skin conditions, the GUI 140 is operated to overlay computer graphics output by the computer graphics generator 156 at locations onto the visual media including the face of the user corresponding to each zone of the plurality of zones of the face of the user, and the computer graphics are depicted with a color associated with the severity level for the skin condition at each of the locations of the face of the user.

The skin advisor platform 130 further includes or has access to databases such as an images/video database 158 that stores the visual media received according to permissions set by the user, a user data database 160 that stores user data (e.g., age, preferences, goals, past purchases, navigation history, etc.) according to permissions set by the user, and a product data database 162 that stores details of products.

In some examples, when permissions are set accordingly by the user, the image recognition module 134 is operated to retrieve visual media of a face of the user from the images/video database 158 (rather than in real-time or substantially real-time from the image capture device 132) for access to pre-existing visual media to process.

The skin advisor platform 130 further includes an input/output (I/O system 164 that couples components of the skin advisor platform 130 to input and output devices of any type. For example, for components of the skin advisor platform 130 that are instantiated at one of the client devices 102 and 104, the I/O system 164 couples to a touch screen display device through which outputs are displayed and user inputs (e.g., touch gestures) are received, the image capture device 132 through which image data is received, and/or a network device through which data is transmitted/received over the network 108. Similarly, for components of the skin advisor platform 130 that are instantiated at the host server device(s) 106, the I/O system 164 couples to a network device through which data is transmitted/received over the network 108.

Figure 5:
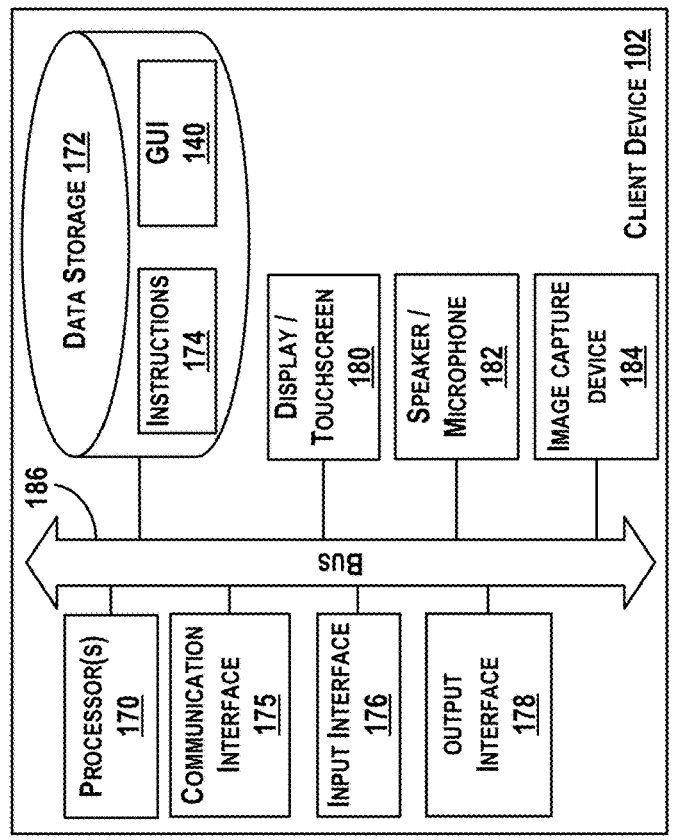
FIG. 5 illustrates a simplified block diagram of the client device, according to an example implementation.

FIG. 5 illustrates a simplified block diagram of the client device 102, according to an example implementation. FIG. 5 does not necessarily show all of the hardware and software modules included in the client device 102, and omits physical and logical connections that will be apparent to one of ordinary skill in the art after review of the present disclosure. Although FIG. 5 illustrates components for the client device 102, the features shown in FIG. 5 are illustrative as components of any client device for use in the networked computer system 100.

The client device 102 includes one or more processor(s) 170, and a non-transitory computer-readable media (data storage) 172 storing instructions 174, which when executed by the one or more processor(s) 170, causes the client device 102 to perform functions (as described below). To perform functions, the client device 102 includes a communication interface 175, an input interface 176, an output interface 178, a display/touchscreen 180, a speaker/microphone 182, and an image capture device 184, and each component of the client device 102 is connected to a communication bus 186. The client device 102 may also include hardware to enable communication within the client device 102 and between the client device 102 and other devices (not shown). The hardware may include transmitters, receivers, and antennas, for example.

The communication interface 175 is a wireless interface and/or one or more wireline interfaces that allow for both short-range communication and long-range communication to one or more networks or to one or more remote devices. Such wireless interfaces provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 175 is configured to receive input data from one or more devices, and configured to send output data to other devices.

The data storage 172 includes or takes the form of memory, such as one or more computer-readable storage media that can be read or accessed by the one or more processor(s) 170. The computer-readable storage media can include volatile and/or non-volatile storage components, such as optical, magnetic, organic or other memory or disc storage, which can be integrated in whole or in part with the one or more processor(s) 170. The non-transitory data storage 172 is considered non-transitory computer readable media. In some examples, the non-transitory data storage 172 can be implemented using a single physical device (e.g., one optical, magnetic, organic or other memory or disc storage unit), while in other examples, the non-transitory data storage 172 can be implemented using two or more physical devices. The non-transitory data storage 172 thus is a computer readable medium, and instructions 174 are stored thereon. The instructions 174 include computer executable code.

The one or more processor(s) 170 is a general-purpose processor or special purpose processor (e.g., digital signal processors, application specific integrated circuits, etc.). The one or more processor(s) 170 receives inputs from the communication interface 175 as well as from other components (the display/touchscreen 180, the speaker/microphone 182, or the image capture device 184), and processes the inputs to generate outputs that are stored in the non-transitory data storage 172. The one or more processor(s) 170 can be configured to execute the instructions 174 (e.g., computer-readable program instructions) that are stored in the non-transitory data storage 172 and are executable to provide the functionality of the client device 102 described herein.

The input interface 176 is used to enter data or commands and can include, for example, a keyboard, a scanner, a user pointing device such as, for example, a mouse, a trackball, or a touch pad, or may further include the touchscreen or microphone.

The output interface 178 outputs information for reporting or storage, and thus, the output interface 178 may be similar to the communication interface 175 and can be a wireless interface (e.g., transmitter) or a wired interface as well.

Figure 6:
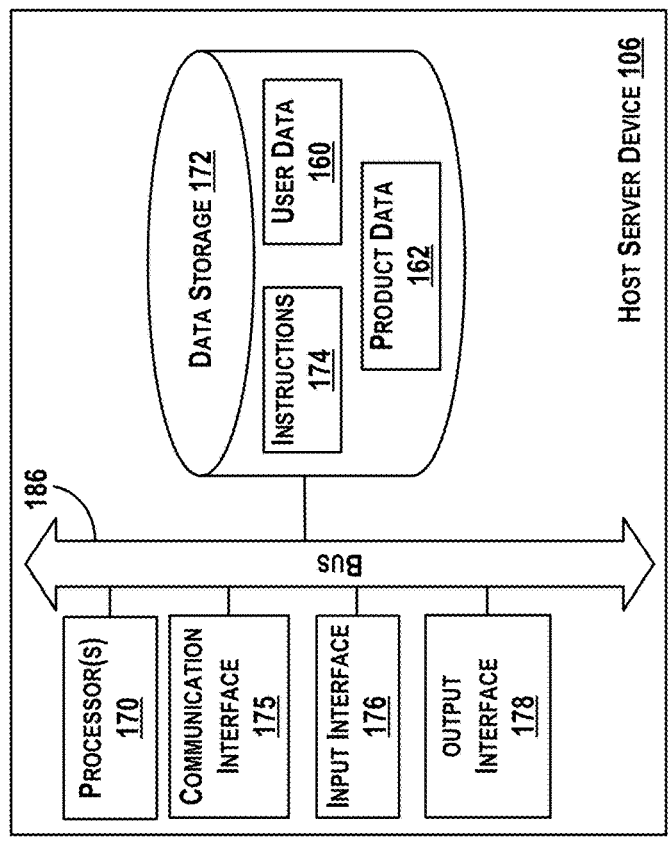
FIG. 6 illustrates a simplified block diagram of the host server device, according to an example implementation.

FIG. 6 illustrates a simplified block diagram of the host server device 106, according to an example implementation. Like the illustration in FIG. 5, FIG. 6 does not necessarily show all of the hardware and software modules included in the host server device 106. Further, similar components illustrated in FIG. 6 that have been described with reference to FIGS. 2-5 are not repeated here.

The host server device 106 can take the form of a server computer, a client computer, a personal computer (PC), a user device, a tablet, a laptop computer, a set-top box (STB), a personal digital assistant (PDA), a thin-client device, or any machine capable of executing a set of instructions (sequential or otherwise) that specify actions to be taken by that machine.

Within one example, in operation, when the instructions 174 are executed by the one or more processor(s) 170 (of the client device 102 or in other examples of the host server device 106, or still in other examples of a combination of the client device 102 and the host server device 106), the one or more processor(s) 170 is caused to perform functions for analyzing skin of a user, such as via the skin advisor platform 130. The functions include requesting, via the GUI 140, visual media including a face of the user, processing the visual media to generate information for each of a plurality of skin conditions of the face of the user and the information comprises a score per each of a plurality of zones of the face of the user per each of the plurality of skin conditions of the face of the user, mapping the score per each of the plurality of zones of the face of the user and for each of the plurality of skin conditions of the face of the user to a severity level associated with the plurality of skin conditions, and for each of the plurality of skin conditions, the GUI 140 overlaying computer graphics at locations onto the visual media including the face of the user corresponding to each zone of the plurality of zones of the face of the user. The computer graphics are depicted with a color associated with the severity level for the skin condition at each of the locations of the face of the user.

FIG. 7-24 illustrate a series of screen captures of an example of the GUI 140 for the skin advisor platform 130. The GUI 140 is be displayed to a user of the client device 102 via a website or an application instantiated at the client device 102. As previously discussed, in some examples, rendering of interface elements and/or images occurs at the host server device 106 that is remote from the client device 102 and is operating as part of the networked computer system 100 or a cloud-based virtual platform. In some examples, an application at the client device 102 performs rendering of interface elements and/or images based on instructions and configurations received from the host server device 106.

Figure 7:
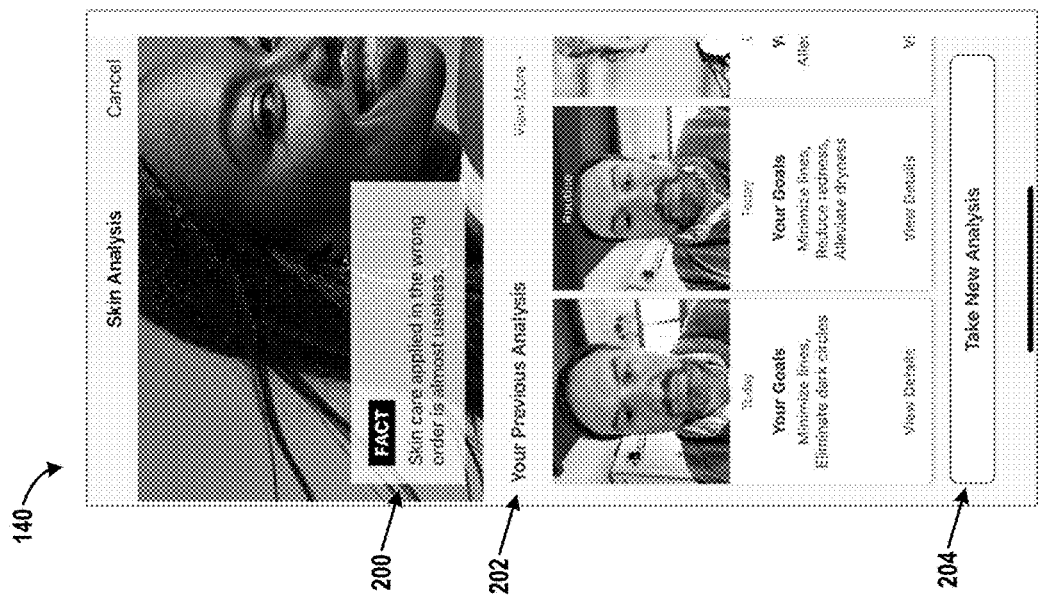
FIG. 7 is a screen capture of an example of the GUI illustrating a "welcome screen," according to an example implementation.

FIG. 7 is a screen capture of an example of the GUI 140 illustrating a "welcome screen," according to an example implementation. Once the application is instantiated and the skin advisor feature is selected, the welcome screen is displayed on the GUI 140 of the client device 102. The welcome screen includes a link 200 to articles with useful related information, a section for previous analysis 202 (described more fully below), and a selectable button 204 to take a new skin analysis.

Figure 8:
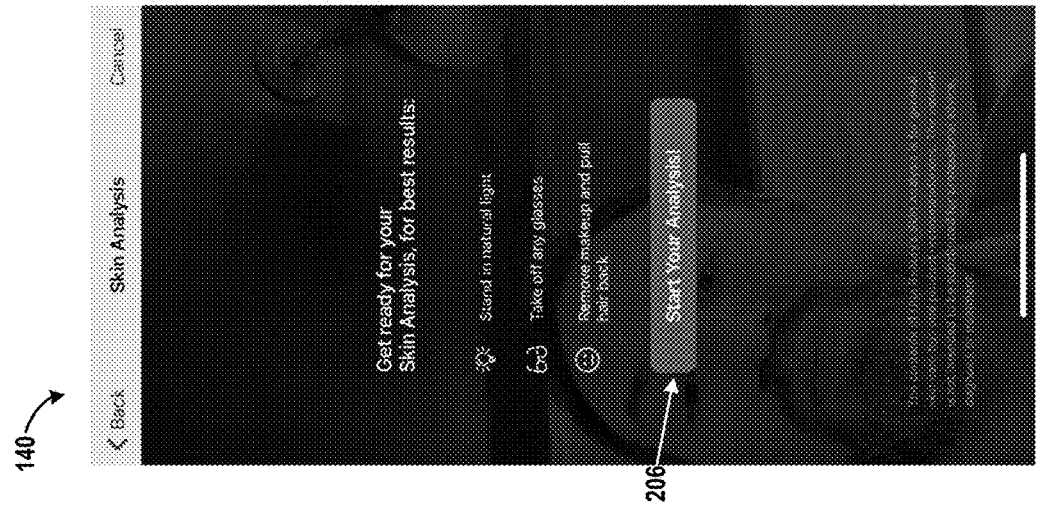
FIG. 8 is a screen capture of an example of the GUI illustrating skin analysis instructions, according to an example implementation.

FIG. 8 is a screen capture of an example of the GUI 140 illustrating skin analysis instructions, according to an example implementation. Once the button 204 is selected, the analysis instructions are displayed on the GUI 140. For best results, the instructions suggest to stand in natural light, remove any eyeglasses, remove any makeup, pull long hair back off the face, and remove any other accessory that could interfere with image analysis. A selectable start button 206 is provided for selection to begin the skin analysis. Note that the analysis instructions screen is semi-transparent, and illustrates in a background a live image feed of the image capture device 132 (e.g., front-facing camera) of the client device 102.

Figures 9, 10, 11:
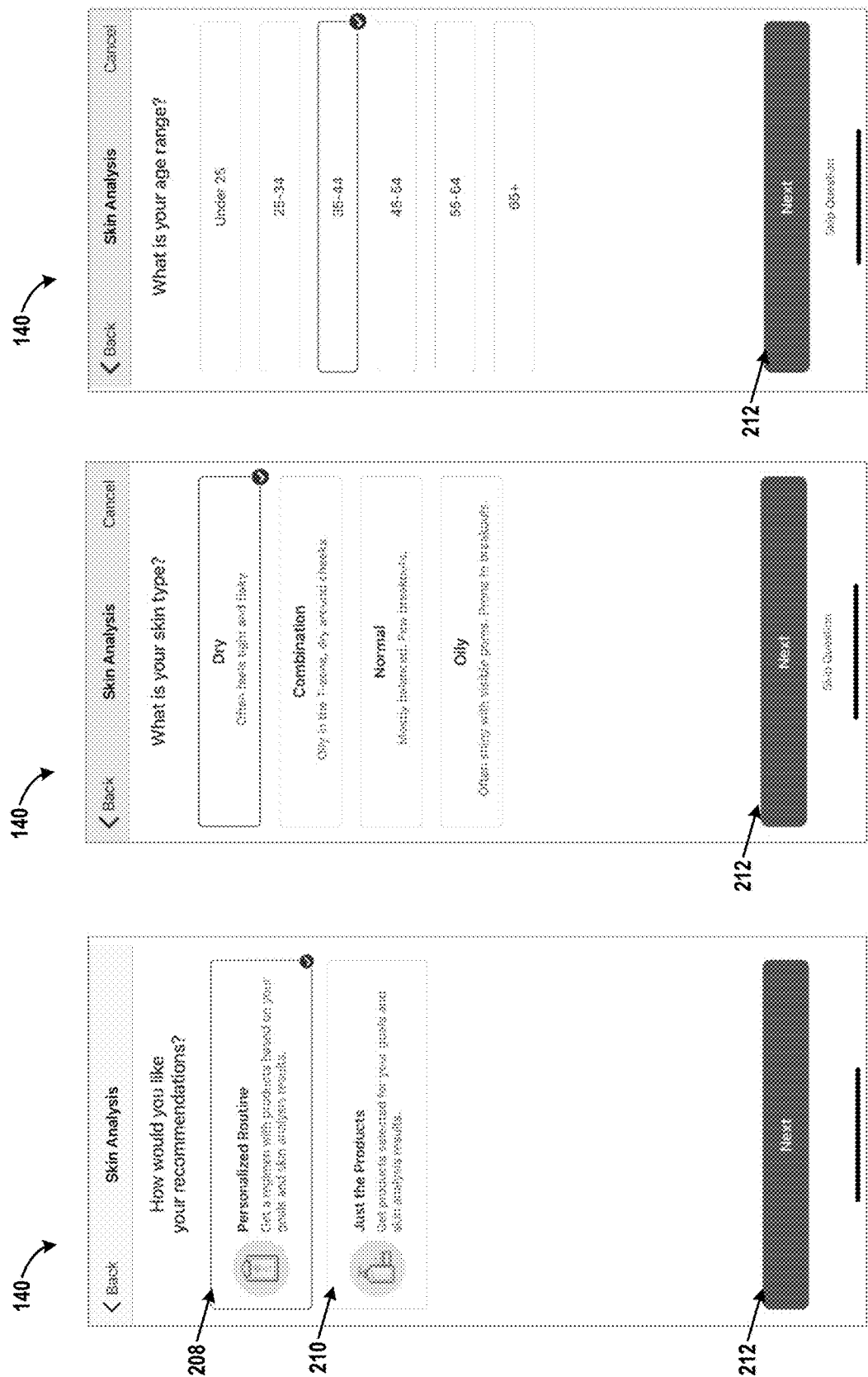
FIG. 9 is a screen capture of an example of the GUI illustrating skin analysis questions for recommendations, according to an example implementation.
FIG. 10 is a screen capture of an example of the GUI illustrating a next set of skin analysis questions, according to an example implementation.
FIG. 11 is a screen capture of an example of the GUI illustrating a next set of skin analysis questions, according to an example implementation.

FIG. 9 is a screen capture of an example of the GUI 140 illustrating skin analysis questions for recommendations, according to an example implementation. For example, an output of the skin analysis includes recommendations for the user, and the GUI 140 allows the user to customize how recommendations are provided, such as recommendations including products that meet skin analysis results, user preferences, and user goals or a personalized routine. The GUI 140 displays a selectable routine button 208 and a selectable product button 210 for input by the user, and then a selectable next button 212 is provided to continue to a next screen.

FIG. 10 is a screen capture of an example of the GUI 140 illustrating a next set of skin analysis questions, according to an example implementation. For example, the GUI 140 next presents questions relating to characteristics of skin type of the user (e.g., dry, oily, normal, etc.).

FIG. 11 is a screen capture of an example of the GUI 140 illustrating a next set of skin analysis questions, according to an example implementation. For example, the GUI 140 asks the user to select an age range.

Figures 12, 13:
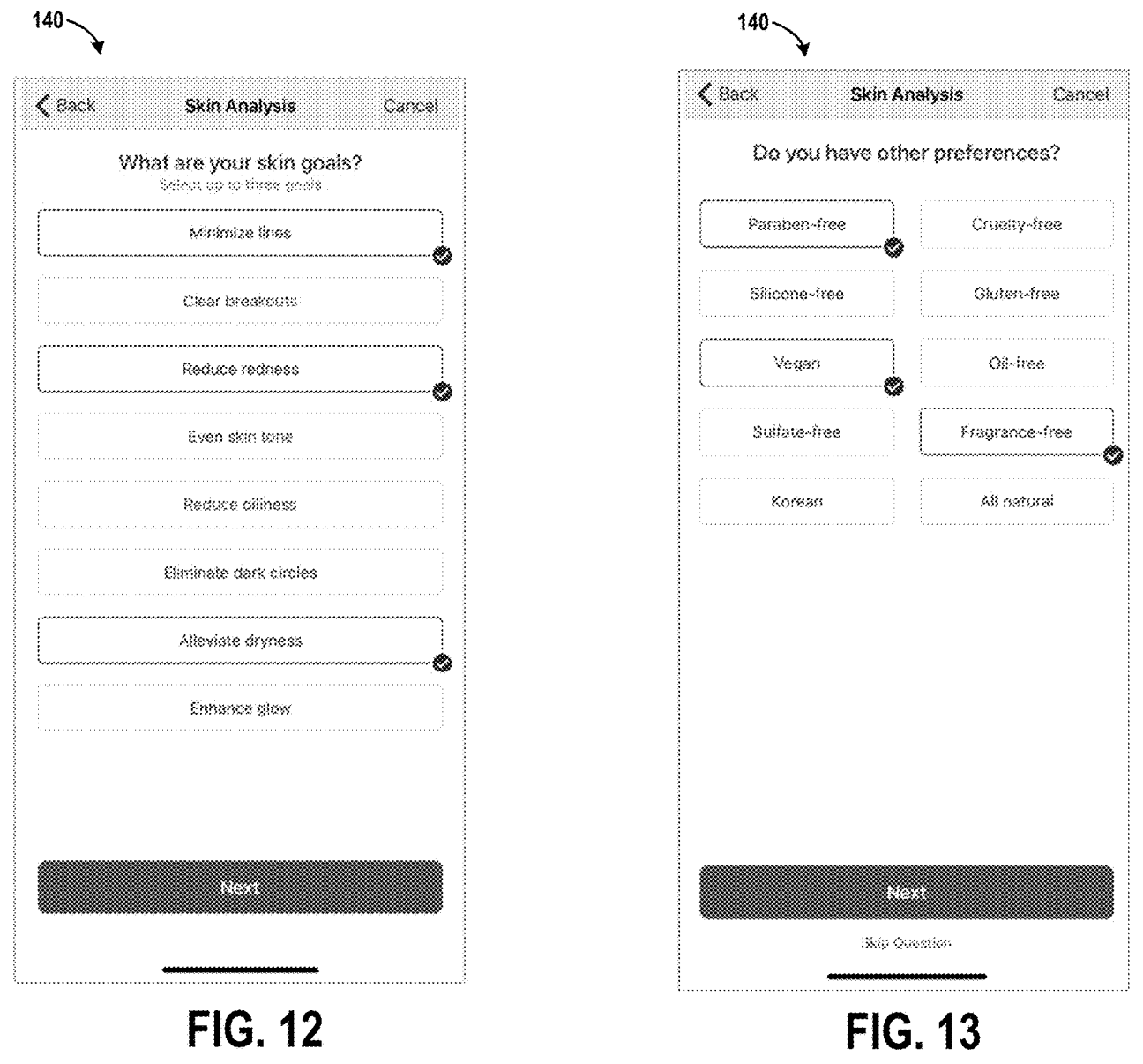

FIG. 12 is a screen capture of an example of the GUI 140 illustrating skin analysis questions for recommendations, according to an example implementation. For example, the GUI 140 asks the user to select skin goals, which relates to characteristics of skin that the user is interested in changing.

FIG. 13 is a screen capture of an example of the GUI 140 illustrating skin analysis questions for recommendations, according to an example implementation. For example, the GUI 140 displays a number of different features for skincare products (e.g., paraben-free, silicone-free, vegan, etc.), and asks the user to select any of the displayed features as preferences to be included in products that can be offered within the recommendations.

Figure 14:
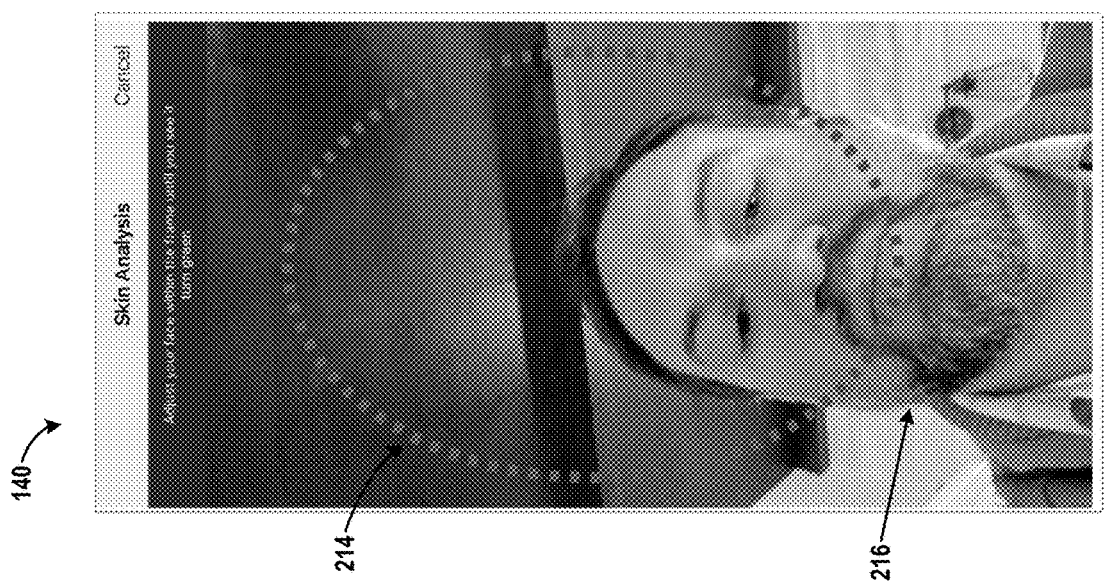
FIG. 14 is a screen capture of an example of the GUI beginning the skin analysis by requesting visual media including a face of a user, according to an example implementation.

FIG. 14 is a screen capture of an example of the GUI 140 beginning the skin analysis by requesting visual media including a face of a user, according to an example implementation. For example, the GUI 140 displays a live visual media feed of the image capture device 132 and spatial position graphics 214 overlaying the live visual media feed of the user to assist with positioning of the face of the user within an area outlined by the spatial position graphics 214. The skin advisor platform 130 evaluates more characteristics of a pose of the face of the user in the visual media, and based on the characteristics of the pose of the face of the user in the visual media indicating a threshold amount of the face of the user is outside the area outlined by the spatial position graphics 214, the GUI 140 requests the user to adjust a position of the face of the user to be within the area outlined by the spatial position graphics 214. In FIG. 14, a portion 216 of the face of the user is outside the area outlined by the spatial position graphics 214, and thus, the GUI 140 displays a message to "Adjust you face within the frame until you see it turn green".

Figure 15:
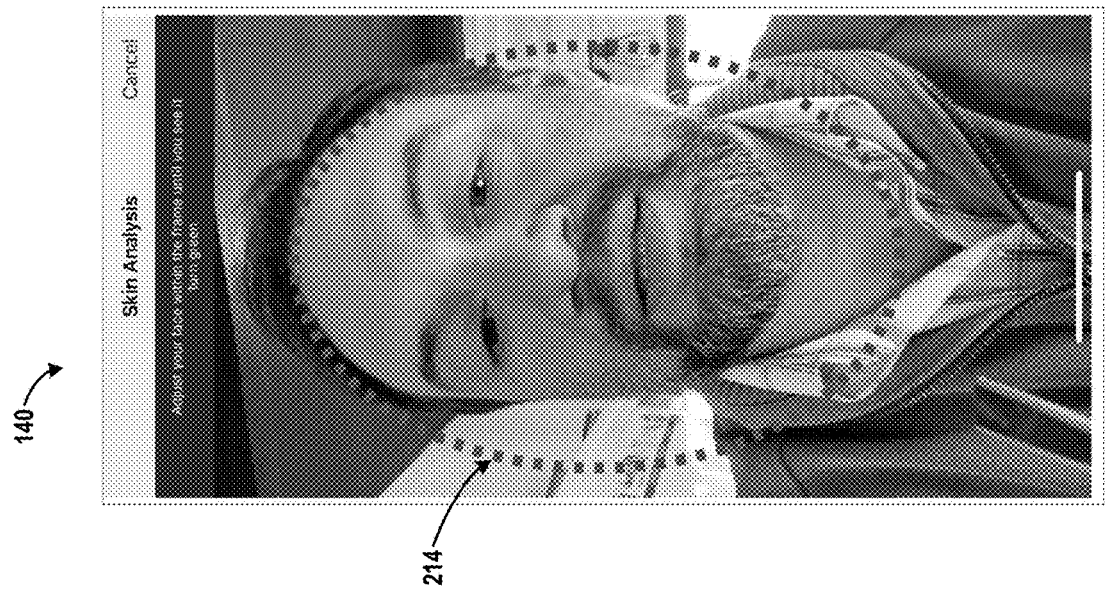
FIG. 15 is a screen capture of an example of the GUI requesting visual media including a face of a user, according to an example implementation.

FIG. 15 is a screen capture of an example of the GUI 140 requesting visual media including a face of a user, according to an example implementation. For example, in FIG. 15, the characteristics of the pose of the face of the user in the visual media indicate the threshold amount of the face of the user is within the area outlined by the spatial position graphics 214, and thus, the GUI 140 displays a color change of the spatial position graphics 214. In FIG. 14, the spatial position graphics 214 are illustrated in a red color, and then in FIG. 15, the spatial position graphics 214 are illustrated in a green color. The threshold amount of the face that needs to be within the area outlined by the spatial position graphics 214 can vary, and is in a range of about 90% to about 100%. Determination of whether the threshold amount of the face of the user is within the area outlined by the spatial position graphics 214 is based on facial feature detection (described more fully below). Once the spatial position graphics 214 turn green, the client device 102 captures the visual media of the face of the user (e.g., captures a still image or clip of video).

Figure 17:
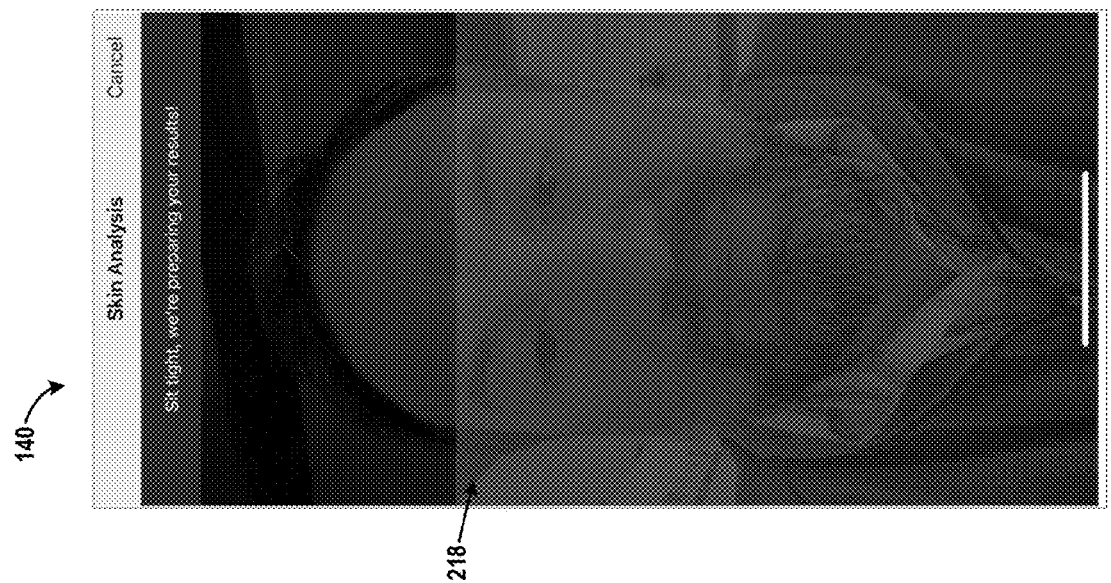
FIG. 17 is a screen capture of another example of animation of graphics displayed by the GUI during skin analysis processing, according to an example implementation.
Figure 16:
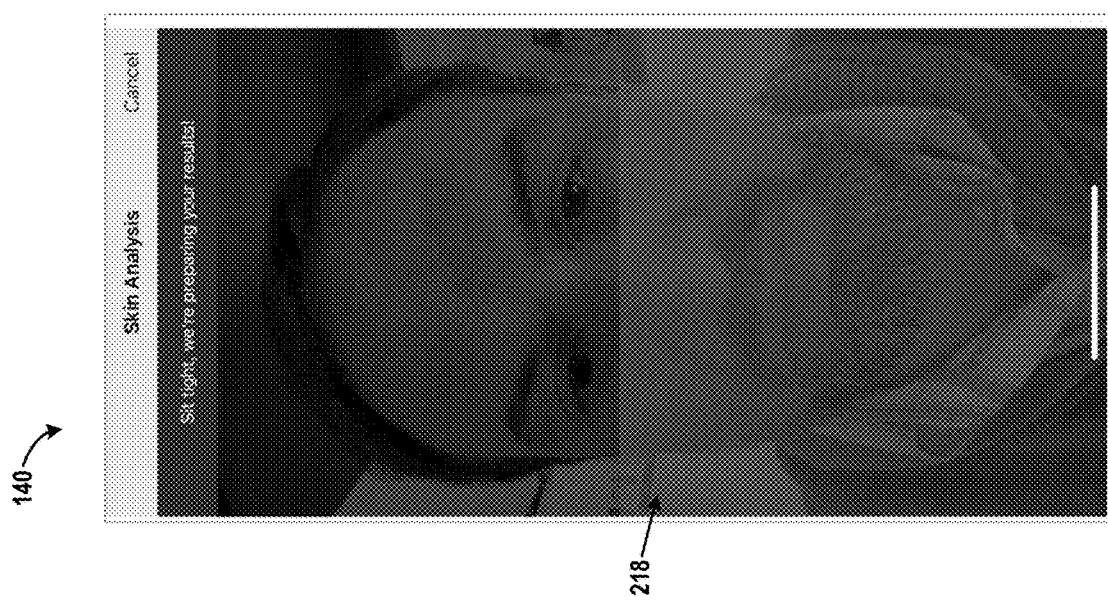
FIG. 16 is a screen capture of an example of animation of graphics displayed by the GUI during skin analysis processing, according to an example implementation.

FIGS. 16-17 are screen captures of an example of animation of graphics displayed by the GUI 140 during skin analysis processing, according to an example implementation. For example, as shown in FIG. 16, the GUI 140 displays a computer graphic 218 overlaying a live visual media feed of the image capture device 132 that is presented in the background. As shown in FIG. 17, the GUI 140 displays the computer graphic 218 in an animated matter moving the computer graphic 218 up and down the display to inform the user that the skin analysis processing is ongoing and not yet completed.

FIGS. 18-22 are screen captures of an example of skin analysis results displayed by the GUI 140 for different skin conditions, according to an example implementation. In each of FIGS. 18-22, the GUI 140 overlays computer graphics at locations onto the visual media including the face of the user corresponding to each zone of the plurality of zones of the face of the user, and the computer graphics are depicted with a color associated with the severity level for the skin condition at each of the locations of the face of the user. The GUI 140 overlays the computer graphics for a single one of the plurality of skin conditions at a time. The various skin conditions can include one or more of discoloration, wrinkles, lines, dark spots, redness, dullness, oiliness, puffiness, and breakouts on the face of the user, and the various zones can include a nose area, a chin area, a cheek area, and a forehead area on the face of the user.

In FIG. 18, the GUI 140 illustrates a skin analysis results screen that includes a section for a still image 220 of the face of the user, an interactive menu bar 222 illustrating the different skin conditions analyzed, and a score description section 224. In this example, the different skin conditions analyzed include lines, redness, eye area, dark spots, and breakouts. In FIG. 18, lines 226 is selected, and the GUI 140 overlays line computer graphics 228/230/232 at locations onto the still image 220 including the face of the user corresponding to each zone of the plurality of zones of the face of the user where such a skin condition has been detected. The line computer graphics 228/230/232 are in a shape that matches detected line features on the face of the user. The GUI 140 further displays a color legend 234 associating a color with a severity level for the skin condition (e.g., none, minimal, moderate, and prominent), and the line computer graphics 228/230/232 are depicted with a color associated with the severity level for the skin condition at each of the locations of the face of the user. The GUI 140 is interactive and allows the image to be expanded or zoomed to see more detail.

In FIG. 19, the GUI 140 illustrates a skin analysis results screen for redness. For example, in FIG. 19, redness 236 is selected, and the GUI 140 overlays redness computer graphics 238/240/242/244/246 at locations onto the still image 220 including the face of the user corresponding to each zone of the plurality of zones of the face of the user where such a skin condition has been detected. For the skin condition redness, the redness computer graphics 238/240/242/244/246 are associated with the different zones of the face (e.g., chin area, cheek areas, nose area, and forehead area), and the redness computer graphics 238/240/242/244/246 are shaped to cover the associated facial zones and displayed in a color associated with the severity level for the skin condition at each of the locations of the face of the user. The redness computer graphics 238/240/242/244/246 are also displayed to be transparent or semi-transparent, and are of a shape that outlines the associated facial zone of the user.

In FIG. 19, the GUI 140 illustrates an example in which, for the respective skin condition of redness, further processing of the visual media can occur to identify a region of interest within a zone. When the region of interest is present, the GUI 140 overlays an additional computer graphic 248 overlaying the redness computer graphic 240 at a location onto the visual media that identifies the region of interest. In this instance, the region of interest indicates a more moderate red spot within a zone that has an overall redness score of minimal.

Figure 20:
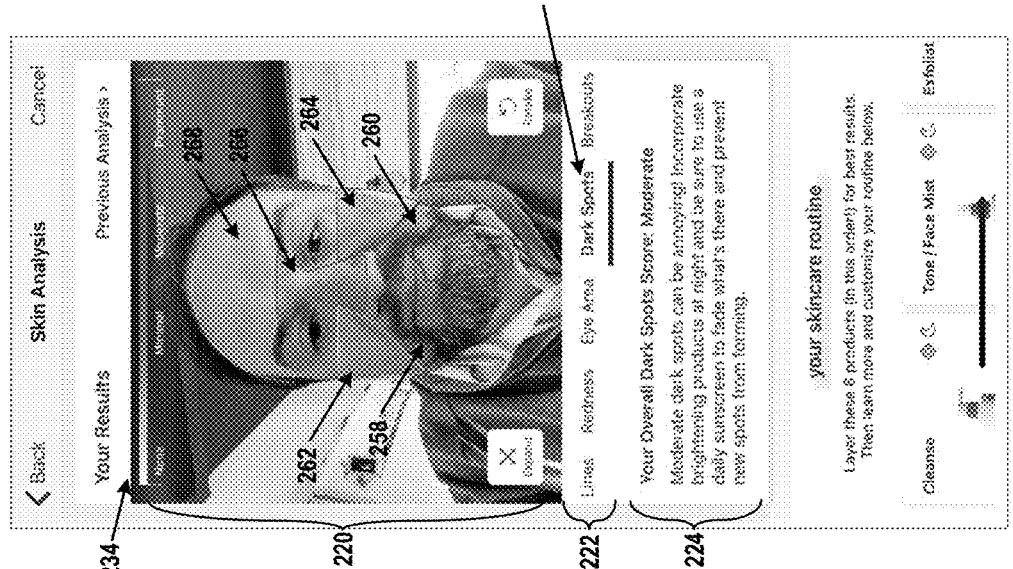
FIG. 20 is a screen capture of an example of skin analysis results displayed by the GUI for eye area, according to an example implementation.

In FIG. 20, the GUI 140 illustrates a skin analysis results screen for eye area. For example, in FIG. 20, eye area 250 is selected, and the GUI 140 overlays eye area computer graphics 252/254 at locations onto the still image 220 including the face of the user corresponding to each zone of the plurality of zones of the face of the user where such a skin condition has been detected. For the skin condition eye area, the eye area computer graphics 252/254 are associated with the zone of the face underneath the eyes, and the eye area computer graphics 250/252 are shaped to cover the associated facial zones and displayed in a color associated with the severity level for the skin condition at each of the locations of the face of the user. For some skin conditions, such as eye area analysis, the severity levels are divided between none and present. The eye area computer graphics 250/252 are also displayed to be transparent or semi-transparent, and are of a shape that outlines the associated facial zone of the user.

Figure 21:
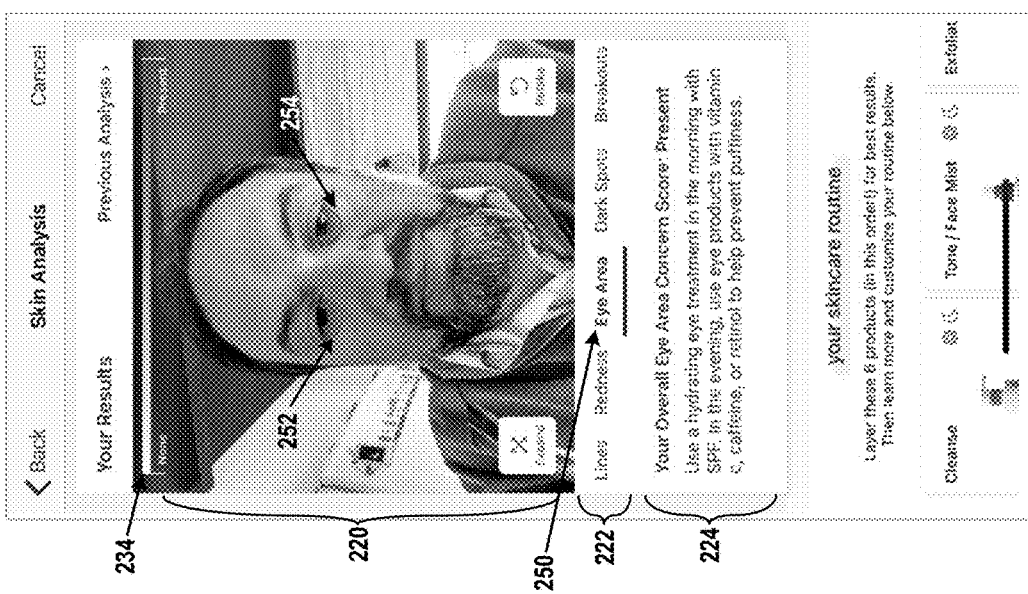
FIG. 21 is a screen capture of an example of skin analysis results displayed by the GUI for dark spots, according to an example implementation.

In FIG. 21, the GUI 140 illustrates a skin analysis results screen for dark spots. For example, in FIG. 21, dark spots 256 is selected, and the GUI 140 overlays dark spot computer graphics 258/260/262/264/266/268 at locations onto the still image 220 including the face of the user corresponding to each zone of the plurality of zones of the face of the user where such a skin condition has been detected. For the skin condition dark spots, the dark spot computer graphics 258/260/262/264/266/268 are associated with the different zones of the face (e.g., chin area, cheek areas, nose area, and forehead area), and the dark spot computer graphics 258/260/262/264/266/268 are shaped to cover the associated facial zones and displayed in a color associated with the severity level for the skin condition at each of the locations of the face of the user. The dark spot computer graphics 258/260/262/264/266/268 are also displayed to be transparent or semi-transparent, and are of a shape that outlines the associated facial zone of the user. The outline of zones used in FIG. 21 differs from outline of zones used in FIG. 19 due to a different skin condition being analyzed and different skin analysis results being displayed.

In FIG. 22, the GUI 140 illustrates a skin analysis results screen for breakouts. For example, in FIG. 22, breakouts 270 is selected, and the GUI 140 overlays a breakout computer graphic 272 at locations onto the still image 220 including the face of the user corresponding to each zone of the plurality of zones of the face of the user where such a skin condition has been detected. For the skin condition breakouts, the breakouts computer graphic 272 is associated an area within one of the different zones of the face (e.g., chin area, cheek areas, nose area, and forehead area), and the breakout computer graphic 272 is shaped to match a detected breakout feature on the face of the user, and displayed in a color associated with the severity level for the skin condition at each of the locations of the face of the user.

FIG. 23 is a screen capture of an example of skin analysis results displayed by the GUI 140 for recommendations, according to an example implementation. For example, the GUI 140 illustrates a summary of the skin analysis results per skin condition, and recommendations below indicating a routine recommendation 274 and product recommendations 276. In FIG. 23, the recommendations are shown for the skin condition of breakouts. The recommendations are generated based on the preferences of the user related to a type or an ingredient of a respective product and goals of the user related to one or more of the plurality of skin conditions (as received by the GUI 140 in interactive functions shown in FIGS. 9-13), and clinical treatment data of the product.

Figure 24:
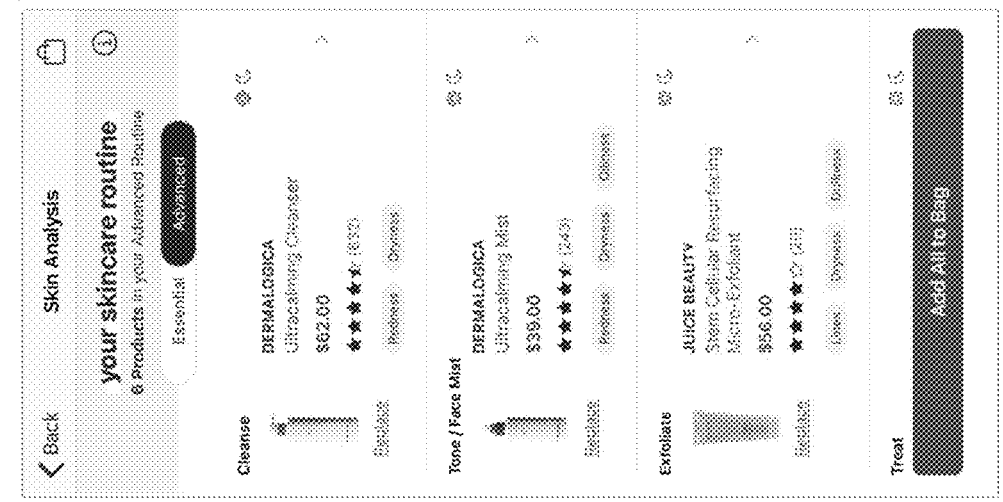
FIG. 24 is a screen capture of an example of skin analysis results displayed by the GUI for previous analysis results, according to an example implementation.

FIG. 24 is a screen capture of an example of skin analysis results displayed by the GUI 140 for previous analysis results, according to an example implementation. As described above in FIG. 7, the GUI 140 illustrates the welcome screen that includes a section for previous analysis 202. Once the previous analysis 202 is selected, the GUI 140 illustrates the screen capture as shown in FIG. 24 to present details of the prior analysis per each skin condition that was analyzed.

Figure 25:
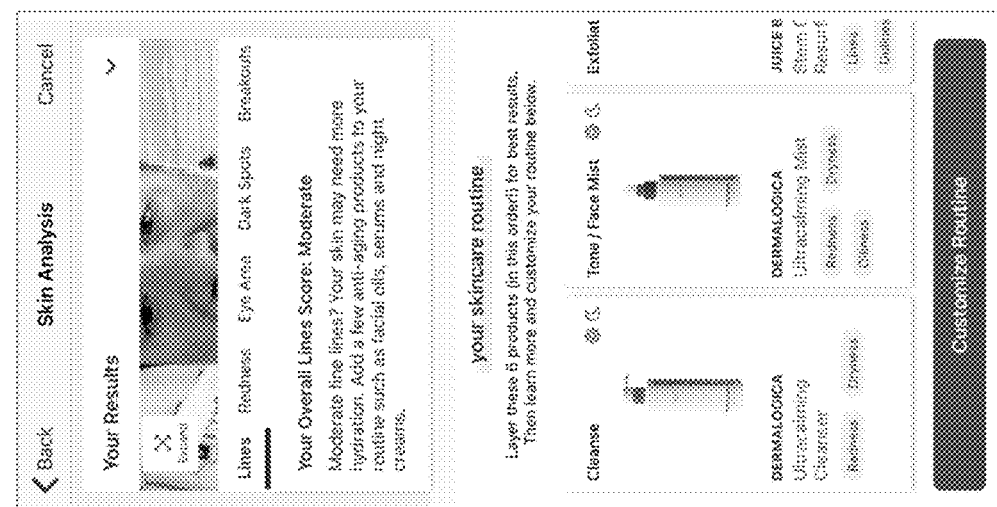
FIG. 25 is a screen capture of an example of further skin analysis results displayed by the GUI for previous analysis results, according to an example implementation.

FIG. 25 is a screen capture of an example of further skin analysis results displayed by the GUI 140 for previous analysis results, according to an example implementation. As a user scrolls down the GUI 140, information for a skincare routine is displayed including recommended products to consider, which each product displayed with corresponding labels indicating the skin condition for which the product may address or provide improvement when used according to the routine.

Figure 26:
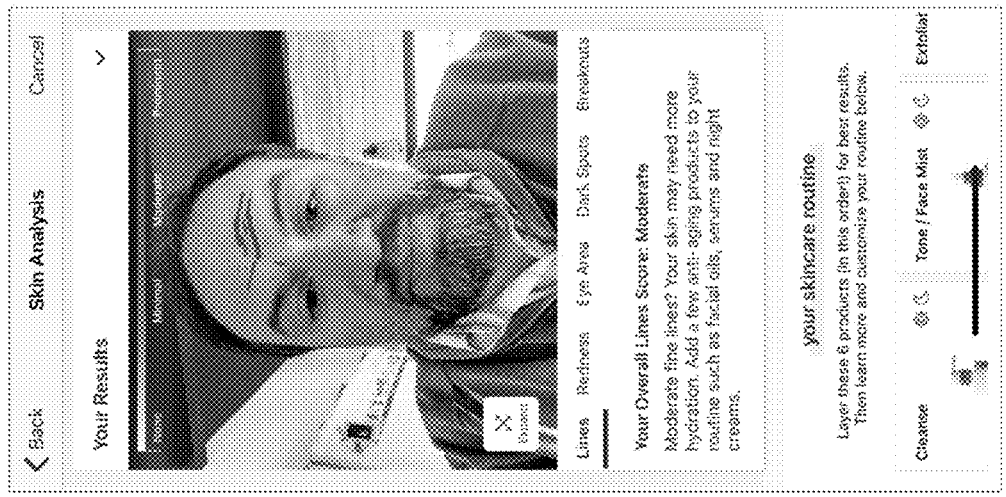
FIG. 26 is a screen capture of an example of customizing a routine as displayed by the GUI, according to an example implementation.

FIG. 26 is a screen capture of an example of customizing a routine as displayed by the GUI 140, according to an example implementation. For example, in FIG. 25, once "customize routine" is selected, the GUI 140 illustrates the screen capture as shown in FIG. 26 to present details of some or all products within the routine. The GUI 140 accepts input for replacing products, and/or enables a user to purchase products as well.

Figure 27:
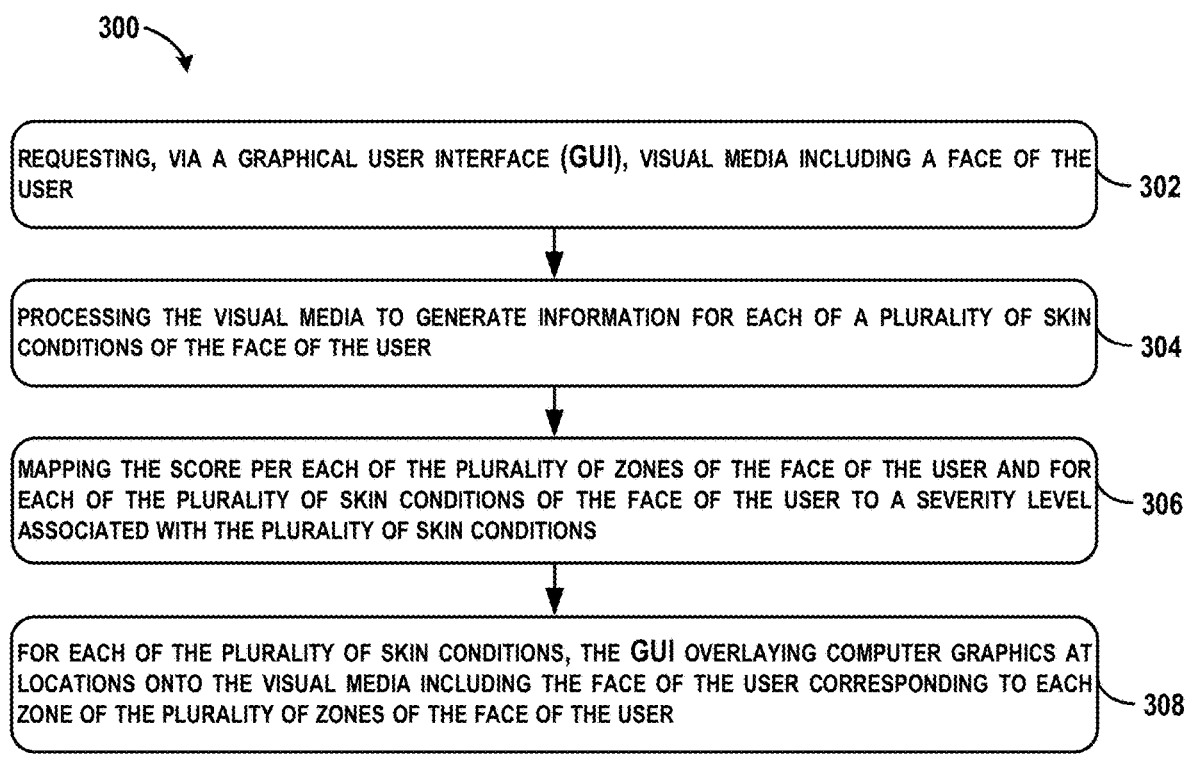
FIG. 27 is a flowchart illustrating an example of a computer-implemented method 300 for analyzing skin of a user, according to an example implementation.

FIG. 27 is a flowchart illustrating an example of a computer-implemented method 300 for analyzing skin of a user, according to an example implementation. Method 300 shown in FIG. 27 presents an example of a method that could be used with the networked computer system 100, the client devices 102 and 104, and/or the host server device(s) 106 shown in FIG. 1 or with the skin advisor platform 130 shown in FIGS. 2-4, for example. Method 300 also presents an example of functions to be performed to generate outputs for display by the GUI 140, as shown in FIGS. 7-26.

Within examples, devices or systems described herein are used or configured to perform logical functions presented in FIG. 27. In some instances, components of the devices and/or systems are configured to perform the functions such that the components are actually configured and structured (with hardware and/or software) to enable such performance. In other examples, components of the devices and/or systems are arranged to be adapted to, capable of, or suited for performing the functions, such as when operated in a specific manner. Method 300 includes one or more operations, functions, or actions as illustrated by one or more of blocks 302-308. Although the blocks are illustrated in a sequential order, these blocks may also be performed in parallel, and/or in a different order than those described herein. In addition, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium includes non-transitory computer readable medium or memory, for example, such as computer-readable media that stores data for short periods of time like register memory, processor cache and Random Access Memory (RAM). The computer readable medium additionally or alternatively includes non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 27, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 302, the method 300 includes requesting, via a graphical user interface (GUI) 140, visual media including a face of the user. In one example, analysis of a skin of the user begins with loading an application on the client device 102 and selecting a skin advisor function on the GUI 140, and after the user provides responses to preliminary questions regarding age, preferences, and goals (e.g., shown in FIGS. 7-13), the GUI 140 requests a scan of the face of the user. In an example where the user has a smartphone with a front-facing camera, the user directs the front-facing to capture an image of the face of the user.

Within an example, block 302 further comprises receiving, via the GUI 140, the visual media including the face of the user, evaluating one or more characteristics of illumination for the visual media, and based on the one or more characteristics of illumination for the visual media not meeting a quality level, requesting, via the GUI 140, a new visual media including the face of the user with an adjustment to lighting in an environment of the user. For example, the skin advisor platform 130 utilizes the light estimation module 136 to measure characteristics of illumination for a digital image include, but not limited to, intensity, direction of light, color temperature, and uniformity of light over the face. In one example, the light estimation module 136 uses light sensors of the client devices 102 and 104 if available. In another example, the light estimation module 136 uses Deep learning face detection algorithms that detect or determine light as a by-product.

When the characteristics of illumination are below a quality level, the GUI 140 will display a message to the user indicating that a new image is requested having an adjustment to lighting in the environment of the user. Various features are considered for determination of the quality level, such as light direction (e.g., frontal or up to a certain threshold in an angle offset from a frontal field of view of the face), color temperature (e.g., neutral versus blue or red), and light intensity (e.g., be above a certain threshold).

Within another example, block 302 further comprises displaying, via the GUI 140, spatial position graphics 214 overlaying a live visual media feed of the user to assist with positioning of the face of the user within an area outlined by the spatial position graphics 214, evaluating one or more characteristics of a pose of the face of the user in the visual media, and based on the one or more characteristics of the pose of the face of the user in the visual media indicating a threshold amount of the face of the user is outside the area outlined by the spatial position graphics 214, requesting, via the GUI 140, the user to adjust a position of the face of the user to be within the area outlined by the spatial position graphics 214. Alternatively, based on the one or more characteristics of the pose of the face of the user in the visual media indicating the threshold amount of the face of the user is within the area outlined by the spatial position graphics 214, displaying, via the GUI, a color change of the spatial position graphics 214.

The spatial position graphics 214 assist a user to aim the image capture device 132 to capture all or substantially all of a user's face, and offers tips for assisting with the face scan (e.g., move camera down). The characteristics of the pose that are evaluated include a position of a head of the user in three spatial locations (along x-axis, y-axis, and z-axis) and along three angles (yaw, pitch, roll), for example. Once a position of the head (based on identified x-axis, y-axis, and z-axis coordinates) is substantially within the spatial position graphics 214, and an orientation of the head (based on the identified yaw, pitch, and roll) is within thresholds, a scan of the face of the user is performed.

Further evaluations of the visual media may also be performed to ensure a high quality image, for example, is being captured. An example of a further evaluation includes determining stability of the detected face/image over time, such as whether the image is jittering or unstable (based on too much movement of the image capture device 132).

To perform functions of block 302, processes for detecting a facial area from a base image, for example, for detecting a human face in an image are initially performed. Any number of facial feature detections processes are performed to detect automatically the face and/or specific features of the face. For example, STASM is an open source software package that can be utilized to return certain landmarks in a face based on a digital image or video. Similarly, DLIB is another open source package that is utilized for performing automated facial feature detection. A person having ordinary skill will recognize that these are two examples of facial feature detection resources that can be utilized and are not intended to be limiting. In certain examples, image pre-processing is applied to aid in the facial feature detection process. For example, segmenting color data in the image, gray scaling the image, equalizing histogram levels, applying Gaussian blurring, applying morphology, etc. After the facial features are detected, a stabilization process is executed to reduce instability of each detected landmark. This could be implemented by standard techniques, such as optical flow computation or Kalman filtering.

Once facial features are detected, data associated with the detected facial features (i.e., region(s) or zones of interest) is output for use in the skin advisor platform 130. In some examples, accuracy of the detected facial features is determined based on a user input indicative of a confirmation that the detected features are accurate. If after performing an initial feature detection, features are not successfully detected or are not confirmed to be accurate, the GUI 140 prompts the user to capture a new image. In some examples, following the initial facial feature detection, a user is presented with an option to provide refining adjustments, such as to adjust region boundaries.

Next, at block 304, the method 300 includes processing the visual media to generate information for each of a plurality of skin conditions of the face of the user. In one example, the information comprises a score per each of a plurality of zones of the face of the user per each of the plurality of skin conditions of the face of the user. In one example, processing at block 304 includes the client device 102 and/or the GUI 140 sending, via the network 108, the visual media to a server (e.g., computer vision server 118) configured to perform computer vision processing, and receiving, from the server via the network 108, the information for each of the plurality of skin conditions of the face of the user. In this example, some image processing is performed off the client device by a server remote from the client device 102.

The number and type of skin conditions analyzed can vary and include any of discoloration, wrinkles, lines, dark spots, redness, dullness, oiliness, puffiness, and breakouts on the face. Each skin condition that is analyzed is analyzed per an identified zone of the face of the user. Zones of the face of the user can include one or more of a nose area, a chin area, a cheek area, and a forehead area on the face of the user.

FIG. 28 is a conceptual illustration of an image 310 of a face of a user divided into zones, according to an example implementation. In FIG. 28, the image 310 is divided into a chin zone 312, cheek zones 314 and 316, a nose zone 318, and a forehead zone 320.

FIG. 29 is another conceptual illustration of the image 310 of the face of the user divided into different zones, according to an example implementation. In FIG. 29, the image 310 is divided into chin zones 322 and 324, the cheek zones 314 and 316, the nose zone 318, and the forehead zone 320.

FIG. 30 is another conceptual illustration of the image 310 of the face with further zones identified, according to an example implementation. In FIG. 30, the image 310 is shown with eye area zones 326 and 328.

Depending on the skin condition being analyzed, zones of the face are selected based on locations on the face for detection of the skin condition. Each of the wrinkle algorithm 144, the redness algorithm 146, the eye algorithm 148, the dark spots algorithm 150, and the breakout algorithm 152 in the skin advisor platform 130 is programmed to analyze certain zones of the face, for example. In one example, the face is divided in a set of predefined zones, and skin conditions tend to manifest with different intensities according to different zones. Relevant zones for each skin condition are then determined based on advice of experts. For example, redness is most likely to be found around the mouth and in the T-zone, whereas sagginess tends to manifest more frequently in the nasolabial fold. Thus, certain zones are associated with different skin conditions.

The score that is output by the skin advisor platform 130 depends on the skin condition being analyzed and the associated algorithm being executed. The score can also be provided at different levels of aggregation, such as per pixel, per region, per zone, or whole face for each skin condition. As an example, pixels of the image are associated with coordinates that map to zones, and values can be associated with each pixel to be indicative of the score. Alternatively, as shown in FIGS. 28-30, zones can be associated with polygons (coordinates of boundaries of the zone), and scores can be associated with the different polygons.

The plurality of skin conditions are in two categories including region conditions or individual conditions, and visual descriptors for each condition are determined. The score for the skin condition is then based on the descriptors. The computation of the descriptors includes (i) the region/location on the face, (ii) geometrical quantities (sizes and shapes), and (iii) color based measurements (e.g., mean color, variance of the color, subzones). The computation of the descriptors can be explicit (e.g., in the case of classical Computer Vision algorithms) or implicit, in the case of modern Deep Learning techniques. The relevant descriptors for each condition will depend on the category (region or location).

Region conditions are conditions that can be associated to continuous regions of the face, for example, redness, dullness, or uneven skin tone. For region condition, descriptors include averages and variances of colors, brightness, and other pixel-based values are calculated to generate the score.

Individual (location) conditions are computed and found at discrete isolated locations, for example, acne, lines/wrinkles, etc. For individual conditions, the geometrical quantities (e.g., shape, depth, length, and overall size) are usually more relevant to determine. In addition, even for the same value of the descriptor, the assigned score might differ depending on the condition. For example, a size of 1 mm could be small for redness, but large for a wrinkle.

Score computation includes assigning weights to the descriptors, which varies based on the condition being analyzed (e.g., the redness algorithm 146 assigns a lower weight for size than the wrinkle algorithm 144), and a machine learning system can be utilized, as trained through use of example images per skin condition, to output scores determined by weights applied to the descriptors.

Referring back to FIG. 27, at block 306, the method 300 includes mapping the score per each of the plurality of zones of the face of the user and for each of the plurality of skin conditions of the face of the user to a severity level associated with the plurality of skin conditions. In one example, a database of manually labeled images is created (offline) for a number of different faces, and each image is labeled with severity levels per condition. The labeled images are utilized by a machine learning system, in which the images of the user are input to identify a mapping of a score to a severity level.

Figure 31:
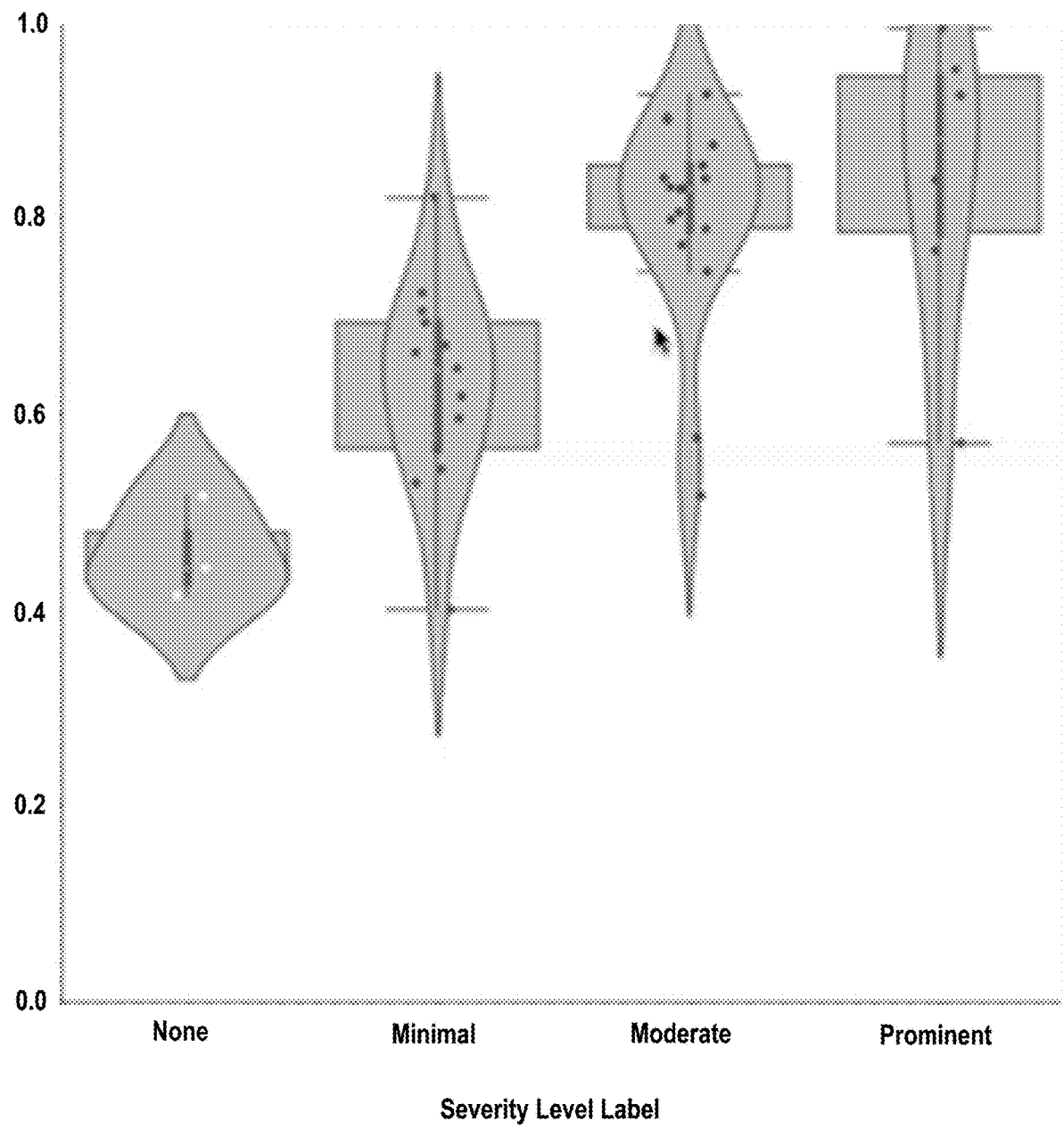
FIG. 31 is an example of a graph of scores to severity levels, according to an example implementation.

FIG. 31 is an example of a graph of scores to severity levels for a respective skin condition, according to an example implementation. The severity levels can be discrete or continuous levels along a spectrum. To identify a threshold between each level, scores and associated labeled severity levels can be graphed for many different images of different faces, and clusters of data are analyzed. A goal is to avoid an erroneous classification of a score into a wrong severity level. The graph will result in clusters of data, and where a density of the cluster falls below a threshold, a demarcation of a severity level can be made. As shown in FIG. 31, a severity level of "none" is associated with scores in a range between 0-0.58, a severity level of "minimal" is associated with scores in a range of about 0.58-0.75, a severity level of "moderate" is associated with scores in a range of about 0.75-0.91, and a severity level of "prominent" is associated with scores in a range of about 0.91-max.

From these ranges, thresholds between severity levels can be adjusted using a machine learning system. A maximum number of levels of severity can be set to be five to provide useful and reliable information to the user and to provide a simple visualization, however, more or fewer levels can be calculated. In some examples, the number of levels can be fixed, but vary for each different skin condition. For example, dullness only has two levels, while dark spots has four levels.

An amount of severity levels chosen for each skin condition can vary depending upon accuracy of detection of the specific condition. Using the graph technique shown in FIG. 31, if a density of the clusters of data is uniform and lacks increases and decreases between different ranges of scores, fewer levels of severity are chosen. If the density of clusters of data is highly differentiated between different ranges of scores, more levels of severity are chosen. Further, as more images are received over time, the machine learning system adjusts a number of severity levels based on an ability to differentiate between scores according to a set accuracy level for the data clusters.

Thus, referring back to FIG. 27, functions at block 306 include computing descriptors for each of the plurality of zones including information related to one or more of characteristics of color per pixel in the visual media and characteristics of geometry for accumulated pixels of similar color, applying a weight to each descriptor, identifying clusters of the descriptors with applied weights between a first threshold and a second threshold such that a range of thresholds is associated with one of a discrete number of severity levels, and associating each of the clusters with a corresponding zone and a corresponding severity level. A number of different severity levels is determined based on how many of the clusters of the descriptors have a number of descriptors above a threshold.

In another example, functions at block 306 include computing descriptors for each of the plurality of zones including information related to one or more of characteristics of color per pixel in the visual media and characteristics of geometry for accumulated pixels of similar color, training a machine learning algorithm, for each of the plurality of skin conditions, with a set of severity level training visual medias, utilizing the machine learning algorithm to apply a weight to each descriptor, identifying clusters of the descriptors with applied weights between a first threshold and a second threshold and a range of thresholds is associated with one of the discrete number of severity levels, and associating each of the clusters with a corresponding zone and a corresponding severity level.

At block 308, the method 300 includes for each of the plurality of skin conditions, the GUI 140 overlaying computer graphics at locations onto the visual media including the face of the user corresponding to each zone of the plurality of zones of the face of the user. The computer graphics are depicted with a color associated with the severity level for the skin condition at each of the locations of the face of the user. The GUI 140 overlays the computer graphics for a single one of the plurality of skin conditions at a time.

In an example, the GUI 140 includes a display screen area for displaying the computer graphics at locations onto the visual media of the face of the user (e.g., the section for the still image 220 of the face of the user) and an interactive menu bar 222 for receiving selection of one of the plurality of skin conditions through input on the GUI 140. Then, based on receiving a selection of one of the plurality of skin conditions through input on the interactive menu bar 222 of the GUI 140, the GUI 140 overlays the computer graphics at locations onto the visual media of the face of the user corresponding to each zone of the plurality of zones of the face of the user for the selected condition. The interactive menu bar 222 includes selectable areas or tabs for each skin condition.

In another example, after receiving selection of a different one of the plurality of skin conditions through input on the interactive menu bar 222 of the GUI 140, the GUI 140 changes overlay of the computer graphics from the first one of the plurality of skin conditions to the selected condition. As described with reference to FIGS. 28-30, relevant zones are determined from a pre-defined list for each skin condition (e.g., choose zones where skin condition most likely present or is detected). Computer graphics can then be displayed as an overlay on top of the still image of the face of the user within the relevant zone.

In a further example, functions of block 308 also include, for a respective skin condition, processing the visual media within each zone of the plurality of zones of the face of the user to identify a region of interest, and generating second computer graphics for overlaying first computer graphics at locations onto the visual media that identify the region of interest. The first computer graphics represent the semi-transparent polygon 240, and the second computer graphics represent the semi-transparent circle 248, as shown in FIG. 19. Zones are fixed locations associated with coordinates of the face whereas regions are variable based on detected skin conditions.

Figure 32:
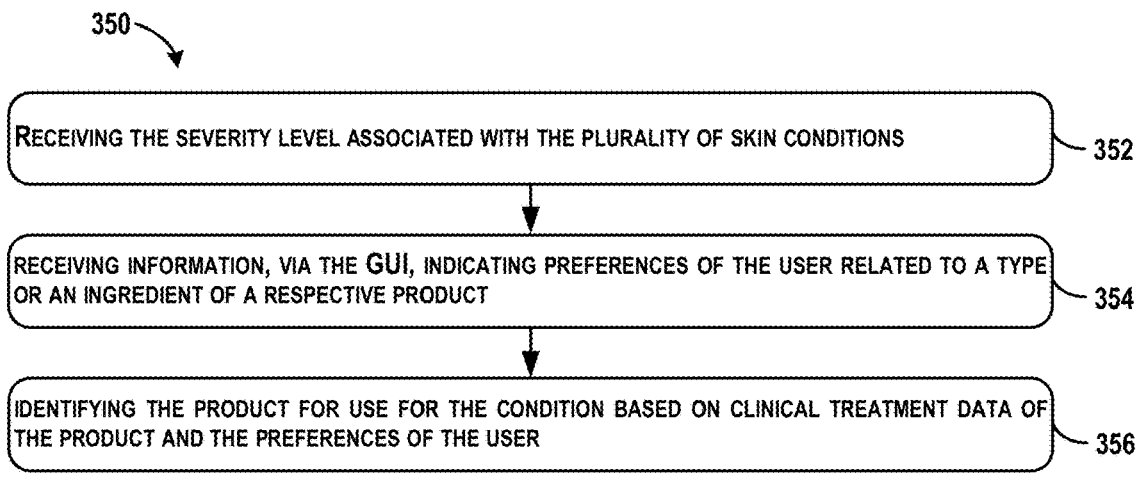
FIG. 32 is a flowchart illustrating an example of a computer-implemented method 350 for providing recommendations to a user, according to an example implementation.
Figure 33:
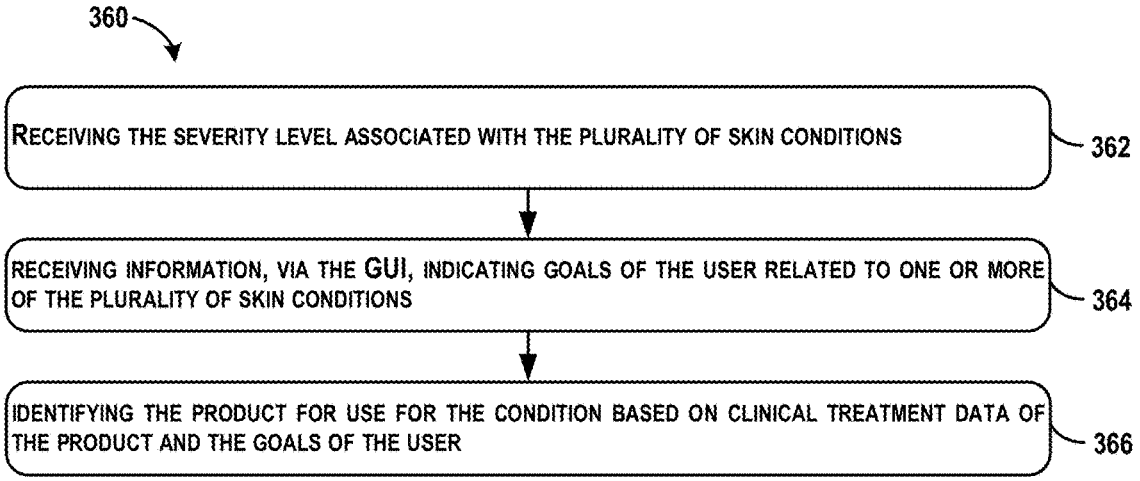
FIG. 33 is a flowchart illustrating an example of another computer-implemented method for providing recommendations to a user, according to an example implementation.

FIG. 32 is a flowchart illustrating an example of a computer-implemented method 350 for providing recommendations to a user, according to an example implementation. Method 350 shown in FIG. 32 presents an example of a method that could be used with the networked computer system 100, the client devices 102 and 104, and/or the host server device(s) 106 shown in FIG. 1 or with the skin advisor platform 130 shown in FIGS. 2-4, for example. Method 350 also presents an example of functions to be performed to generate outputs for display by the GUI 140, as shown in FIG. 23-26.

At block 352, the method 350 includes receiving the severity level associated with the plurality of skin conditions. For example, the severity level is received at the recommendation server 120, as shown in FIG. 1. At block 354, the method 350 includes receiving information, via the GUI 140, indicating preferences of the user related to a type or an ingredient of a respective product, such as shown in FIG. 13. At block 356, the method 350 includes identifying the product for use for the condition based on clinical treatment data of the product and the preferences of the user. In this example, a recommended product for use to treat the identified skin condition takes into account also specific customized preferences of the user of types of products and/or ingredients of products that the user has indicated for further filtering of the products offered in the recommendation FIG. 32 is a flowchart illustrating an example of another computer-implemented method 360 for providing recommendations to a user, according to an example implementation. Method 360 shown in FIG. 32 presents an example of a method that could be used with the networked computer system 100, the client devices 102 and 104, and/or the host server device(s) 106 shown in FIG. 1 or with the skin advisor platform 130 shown in FIGS. 2-4, for example. Method 360 also presents an example of functions to be performed to generate outputs for display by the GUI 140, as shown in FIG. 23-26.

At block 362, the method 360 includes receiving the severity level associated with the plurality of skin conditions. For example, the severity level is received at the recommendation server 120, as shown in FIG. 1. At block 364, the method 360 includes receiving information, via the GUI 140, indicating goals of the user related to one or more of the plurality of skin conditions, such as shown in FIG. 12. At block 366, the method 360 includes identifying the product for use for the condition based on clinical treatment data of the product and the goals of the user. In this example, a recommended product for use to treat the identified skin condition takes into account also specific customized goals of the user for further filtering of the products offered in the recommendation.

In an example, for recommendations based on goals of a user, the recommendation server 120 can map a goal to a set of conditions and then map the conditions to products indicated as being clinically successful in treating the condition. For example, a user selects as a goal to reduce or minimize lines. The goal to reduce lines is associated with the condition of wrinkles, and products associated with treating wrinkles include products high in hydration, for example.

Figure 34:
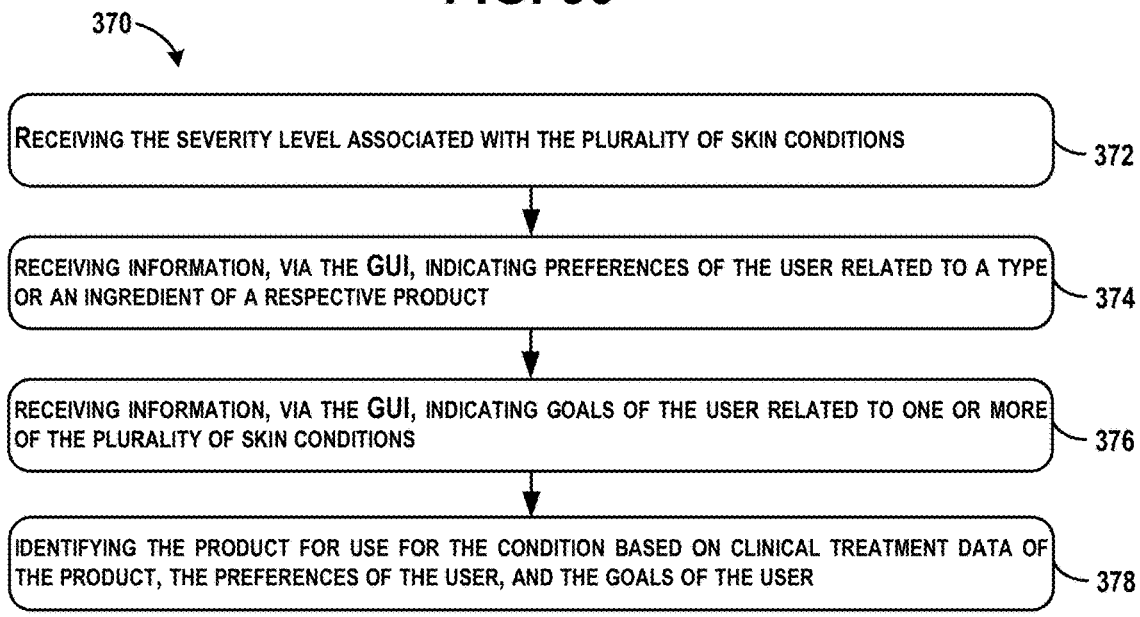
FIG. 34 is a flowchart illustrating an example of another computer-implemented method for providing recommendations to a user, according to an example implementation.

FIG. 34 is a flowchart illustrating an example of another computer-implemented method 370 for providing recommendations to a user, according to an example implementation. Method 370 shown in FIG. 34 presents an example of a method that could be used with the networked computer system 100, the client devices 102 and 104, and/or the host server device(s) 106 shown in FIG. 1 or with the skin advisor platform 130 shown in FIGS. 2-4, for example. Method 370 also presents an example of functions to be performed to generate outputs for display by the GUI 140, as shown in FIG. 23-26.

At block 372, the method 370 includes receiving the severity level associated with the plurality of skin conditions. For example, the severity level is received at the recommendation server 120, as shown in FIG. 1. At block 374, the method 370 includes receiving information, via the GUI 140, indicating preferences of the user related to a type or an ingredient of a respective product, such as shown in FIG. 13. At block 376, the method 370 includes receiving information, via the GUI 140, indicating goals of the user related to one or more of the plurality of skin conditions, such as shown in FIG. 12. At block 378, the method 370 includes identifying the product for use for the condition based on clinical treatment data of the product, the preferences of the user, and the goals of the user. In this example, a recommended product for use to treat the identified skin condition takes into account all specific customized preferences and goals of the user for further filtering of the products offered in the recommendation.

In further examples, any of the methods 350, 360, and 370 further include functions of any number or types of follow-up activities (informative items) that could be included as recommendations, such as products to purchase, routines to execute, services to schedule, video content to view, etc.

In further examples, any of the methods 350, 360, and 370 further include functions of identifying a beauty routine or a beauty service to execute for the condition, and the beauty routine is based on a time of day of execution of the beauty routine or based on a time of year of execution of the beauty routine. A routine is a regimen with products for use based on goals and skin analysis results, and can depend on the severity levels, the ingredients of the products, and the types of the products. There also are different routines for different times of the day (morning versus evening) or different routines for different weather and seasons (e.g., during summer, it might include using a product with a different sun protection factor (SPF)), for example.

The recommendation server 120 matches the recommendations (e.g., product(s)) with severity level of the skin condition, and the goals and preferences selected using a database of labeled products. Further customized mapping can take into account past user purchases, best-selling products, trends, and promotions by the recommendation server 120 accessing the analytic(s) server 114. A first mapping of a product identifies a product that has been identified to address clinically the identified skin condition at the associated severity level, and then the preferences and goals further assist to tune the recommendation to a fully customized recommendation for the specific user. Two users may have the skin condition of redness at a moderate severity level; however, each may have different goals or preferences leading to different products being recommended to each user.

As shown in FIGS. 25-26, recommendations are displayed to the user in the GUI 140 and the methods 350, 360, 370 describe functions for determinations of the specific recommendations.

Figure 35:
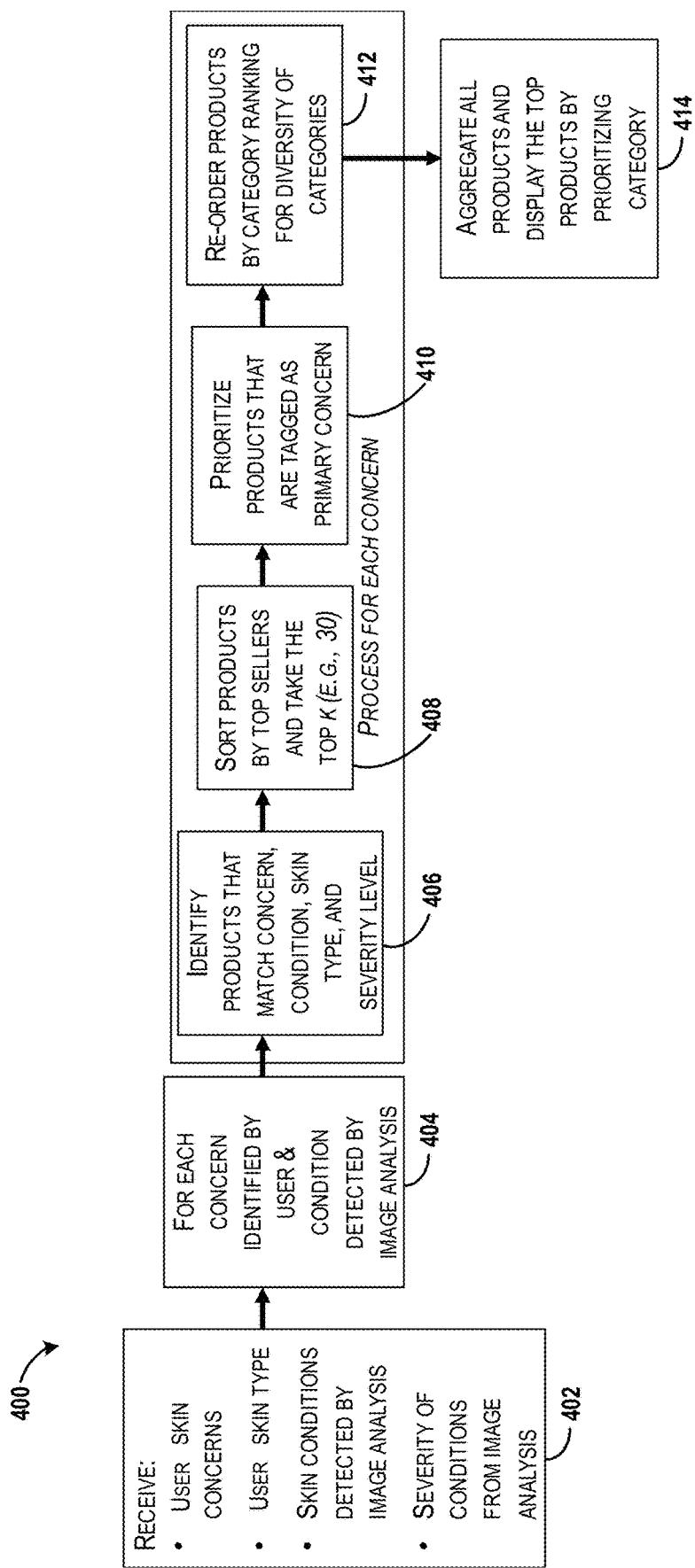
FIG. 35 is another flowchart illustrating an example of another computer-implemented method for providing recommendations to a user, according to an example implementation.

FIG. 35 is another flowchart illustrating an example of another computer-implemented method 400 for providing recommendations to a user, according to an example implementation. Method 400 shown in FIG. 35 presents an example of a method that could be used with the networked computer system 100, the client devices 102 and 104, and/or the host server device(s) 106 shown in FIG. 1 or with the skin advisor platform 130 shown in FIGS. 2-4, for example. Method 400 also presents an example of functions to be performed to generate outputs for display by the GUI 140, as shown in FIG. 23-26.

At block 402, the method 400 includes receiving the user skin concerns and user skin type (e.g., via the GUI 140 as shown in FIGS. 9-13), the skin conditions detected by image analysis (e.g., as performed by some functions described in FIG. 27), and a severity of the skin conditions from the image analysis. Next, as indicated at block 404, a series of functions are performed for each concern identify by the user and for each skin condition detected by the image analysis.

For example, the GUI 140 product recommendations reflect how the process of recommendations happens in real life. Skin care recommendations take into account goals each user wants to achieve, and the skin advisor platform 130 combines skin analysis with the skin goals of each of the user to recommend optimal products. The skin advisor platform 130 balances user goals with skin analysis results identifying skin conditions and severities of such conditions that match to products and product ingredients. Severities from the skin analysis are specifically matched with product ingredients that are more adequate for the need. For users in which data is available, recommendations consider past purchases as well to provide a personalized set of skin care products that address the identified skin conditions and skin goals. Thus, at block 406, the method 400 includes identifying products that match concerns, conditions, skin type, and severity level for the user.

Recommendations are further enhanced by providing compatible product recommendations depending on ingredients. For example, products are tagged or labeled for a concern, body part, skin type, and severity level. Once products are identified, the method 400 includes, at block 408, sorting the products by top sellers to produce a ranking of products (e.g., top 30).

Following, at block 410, the method 400 includes prioritizing products that are tagged as addressing the primary concerns. At block 412, the method 400 includes re-ordering products by category ranking to produce a listing of products for a diversity of categories (e.g., to provide an assortment of products).

At block 414, the method 400 includes aggregating all products and displaying, via the GUI 140, the top products by prioritized categories. Each product that is displayed includes a label for the concern and/or skin condition that the product is recommended to address, as shown in FIG. 25-26 (e.g., product "Ultracalming Cleanser" labeled for "redness" and "dryness").

The method 400 provides an example of functionality for identifying a sequence of products for use in an identified order and at a certain time to address user concerns and identified skin conditions. Different product categories are used to identify skin products, such as cleansers, toners, moisturizers, SPF, etc., and recommendations are provided as a set of grouped products selected from the different product categories resulting in routines. Instructions are further provided along with each of the products recommended such as cadence for use, time of day, and order of application. In addition, a customization option of the routine is provided (e.g., as shown in FIGS. 25-26) that allows the user to select a shorter (essential) or longer routine (advanced), exchange products, or filter out products, for example.

As mentioned, and illustrated in FIG. 24, a profile of the user can be saved that includes the skin analysis. As an example, the method 300 of FIG. 27 can optionally include functions of storing, in non-transitory computer readable media, a first skincare analysis record including information for the computer graphics and the score per each of the plurality of zones of the face of the user and for each of the plurality of skin conditions of the face of the user mapped to the severity level, and the first skincare analysis record is associated with a first date. Then, the method 300 can include generating a second skincare analysis record associated with a second date, and based on the first date being within a threshold number of days of the second date, combining the first skincare analysis record and the second skincare analysis record into an accumulated skincare analysis record.

In this example, when the skincare analyses are close in time, there is unlikely to be much difference and the alternate visual media can be used to generate a more robust record. As a specific example, if several analyses close in time or on same day are performed and a prominent redness skin condition is determined three times and one moderate redness condition is determined one time, then the overall result can be associated with the prominent redness skin condition.

In another example, subsequent skin analyses can be performed and compared with the prior analysis. As an example, the method 300 of FIG. 27 can optionally include functions of storing, in non-transitory computer readable media, a first skincare analysis record including information for the computer graphics and the score per each of the plurality of zones of the face of the user and for each of the plurality of skin conditions of the face of the user mapped to the severity level and the first skincare analysis record is associated with a first date, generating a second skincare analysis record associated with a second date; and comparing the first skincare analysis record with the second skincare analysis record to identify a trend for each of the plurality of skin conditions of the face of the user.

In this example, a trend indicating a score decreasing overtime can be associated with an improvement in the identified skin condition. A "skin metric" is further generated, in some examples, that is a combination of improvement in trends of skin conditions, and the skin advisor platform 130 monitors the skin metric to identify content, opportunities, and experiences to offer to the user. The skin metric may be based on 100 and a range of 0-20 is associated with minimal improvement, a range of 20-40 is associated with fair improvement, a range of 40-60 is associated with good improvement, and so on. The skin metric relates to behavior of the user with respect to skincare measurement, and the skin advisor platform uses the skin metric as a trigger for the client device 102 to execute other functions of the GUI 140. Other functions can include unlocking unique content, earning access to personal tutorials, etc.

In another example, the skin metric is utilized to identify patterns of skincare management and user behaviors. For instance, the skin advisor platform 130 can identify patterns, such identifying scenarios where a user that uses some cream for acne results in improvement of the skin condition for breakouts, but shows a deterioration in a skin condition for wrinkles or redness that may be due to less hydration in the skin from use of the cream.

As still another example, the skin advisor platform 130 can identify improvement in a skin condition over time, and identify whether an amount of improvement is slows down as a factor to consider for user behavior. The factor can be input to the recommendation server 120 as a further data point for consideration.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples describe different advantages as compared to other advantageous examples. The example or examples selected are chosen and described to explain the principles of the examples, the practical application, and to enable others of ordinary skill in the art to understand the disclosure for various examples with various modifications as are suited to the particular use contemplated.

Having described the subject matter of the present disclosure in detail and by reference to specific examples thereof, it is noted that the various details disclosed herein should not be taken to imply that these details relate to elements that are essential components of the various examples described herein, even in cases where a particular element is illustrated in each of the drawings that accompany the present description. Further, it will be apparent that modifications and variations are possible without departing from the scope of the present disclosure, including, but not limited to, examples defined in the appended claims. More specifically, although some aspects of the present disclosure are identified herein as preferred or particularly advantageous, it is contemplated that the present disclosure is not necessarily limited to these aspects.

Moreover, while some examples have been described in the context of fully functioning computers and computer systems, those skilled in the art will appreciate that various examples are capable of being distributed as a program product in a variety of forms, and that the disclosure applies equally regardless of a particular type of machine or computer-readable media used to effect the distribution.

Further examples of machine-readable storage media, machine-readable media, or computer-readable (storage) media include, but are not limited to, recordable type media such as volatile and non-volatile memory devices, floppy and other removable drives, hard drives, optical disks (e.g., Compact Disk Read-Only Memory (CD ROMS), Digital Versatile Disks, (DVDs), etc.), among others, and transmission type media such as digital and analog communication links.

For the purposes of describing and defining examples herein, it is noted that terms "substantially" or "about" are utilized herein to represent an inherent degree of uncertainty attributed to any quantitative comparison, value, measurement, or other representation. The terms "substantially" and "about," when utilized herein, represent the degree by which a quantitative representation may vary from a stated reference without resulting in a change in a basic function of the subject matter at issue.

What is claimed is:

1. A computer-implemented method for analyzing skin of a user, comprising:
   requesting, via a graphical user interface (GUI), visual media including a face of the user;
   processing the visual media to generate information for each of a plurality of skin conditions of the face of the user, wherein the information comprises a score per each of a plurality of zones of the face of the user per each of the plurality of skin conditions of the face of the user, wherein the plurality of skin conditions comprise a region condition associated to a continuous region of the face and an individual condition associated with a discrete location of the face;
   mapping the score per each of the plurality of zones of the face of the user and for each of the plurality of skin conditions of the face of the user to one of a plurality of severity levels associated with the plurality of skin conditions by:
      computing first descriptors for the region condition, wherein the first descriptors include characteristics of color per pixel in the visual media;
      computing second descriptors for the individual condition, wherein the second descriptors include characteristics of geometry for accumulated pixels of similar color;
      applying a weight to each of the first descriptors and the second descriptors that is varied based on one of the plurality of skin conditions being analyzed;
      identifying clusters of the first descriptors and clusters of the second descriptors with applied weights between a first threshold and a second threshold, wherein the one of the plurality of severity levels is one of a discrete number of severity levels and wherein a range of thresholds is associated with one of the discrete number of severity levels; and
      associating each of the clusters with a corresponding zone and a corresponding severity level; and
   for each of the plurality of skin conditions, the GUI overlaying computer graphics at locations onto the visual media including the face of the user corresponding to each zone of the plurality of zones of the face of the user, wherein the computer graphics are depicted with a color associated with the one of the plurality of severity levels for the skin condition at each of the locations of the face of the user.

2. The method of claim 1, wherein, for a respective skin condition of the plurality of skin conditions, the GUI overlaying computer graphics comprises the GUI overlaying first computer graphics, and the method further comprises:
   for the respective skin condition, processing the visual media within each zone of the plurality of zones of the face of the user to identify a region of interest; and
   generating second computer graphics for overlaying the first computer graphics at the locations onto the visual media that identify the region of interest.

3. The method of claim 1, wherein processing the visual media comprises processing the visual media to generate information for one or more of discoloration, wrinkles, lines, dark spots, redness, dullness, oiliness, puffiness, and breakouts on the face of the user per each of a nose area, a chin area, a cheek area, and a forehead area on the face of the user.

4. The method of claim 1, further comprising:
   determining a number of different severity levels of the plurality of severity levels based on how many of the clusters of the first descriptors and the clusters of the second descriptors have a number of descriptors above a threshold.

5. The method of claim 1, wherein the one of the plurality of severity levels is one of the discrete number of severity levels along a spectrum, and wherein mapping the score comprises:
   training a machine learning algorithm, for each of the plurality of skin conditions, with a set of severity level training visual medias;
   utilizing the machine learning algorithm to apply the weight to each descriptor.

6. The method of claim 1, wherein the GUI overlaying the computer graphics comprises the GUI overlaying the computer graphics for a single occurrence one of the plurality of skin conditions at a time.

7. The method of claim 1, wherein the GUI includes a display screen area for displaying the computer graphics at the locations onto the visual media of the face of the user and an interactive menu bar for receiving a selection among the plurality of skin conditions through input on the GUI, and the method comprises:
   based on receiving the selection among the plurality of skin conditions through the input on the interactive menu bar of the GUI, overlaying the computer graphics at the locations onto the visual media of the face of the user corresponding to each zone of the plurality of zones of the face of the user for the selection among the plurality of skin conditions.

8. The method of claim 1, wherein the GUI includes a display screen area for displaying the computer graphics at the locations onto the visual media of the face of the user and an interactive menu bar for receiving a selection among the plurality of skin conditions through input on the GUI,
   and wherein the GUI overlaying computer graphics at the locations onto the visual media of the face of the user comprises the GUI overlaying computer graphics for a first of the plurality of skin conditions,
   and the method further comprises:
   based on receiving the selection among the plurality of skin conditions through the input on the interactive menu bar of the GUI, changing an overlay of the computer graphics from the first of the plurality of skin conditions to the selection among the plurality of skin conditions.

9. The method of claim 1, further comprising:
   receiving, via the GUI, the visual media including the face of the user;
   evaluating one or more characteristics of illumination for the visual media;
   based on the one or more characteristics of illumination for the visual media not meeting a quality level, requesting, via the GUI, a new visual media including the face of the user with an adjustment to lighting in an environment of the user.

10. The method of claim 1, further comprising:
displaying, via the GUI, spatial position graphics overlaying a live visual media feed of the user to assist with positioning of the face of the user within an area outlined by the spatial position graphics;
evaluating one or more characteristics of a pose of the face of the user in the visual media;
based on the one or more characteristics of the pose of the face of the user in the visual media indicating a threshold amount of the face of the user is outside the area outlined by the spatial position graphics, requesting, via the GUI, the user to adjust a position of the face of the user to be within the area outlined by the spatial position graphics; and
based on the one or more characteristics of the pose of the face of the user in the visual media indicating the threshold amount of the face of the user is within the area outlined by the spatial position graphics, displaying, via the GUI, a color change of the spatial position graphics.

11. The method of claim 1, further comprising:
based on the one of the plurality of severity levels associated with the plurality of skin conditions, the GUI displaying information related to one or more of a product for use for the condition, a beauty routine to execute for the condition, and a service to schedule for the one of the plurality of skin conditions.

12. The method of claim 11, further comprising:
receiving information, via the GUI, indicating preferences of the user related to a type or an ingredient of the product;
identifying the product for use for the one of the plurality of skin conditions based on clinical treatment data of the product and the preferences of the user.

13. The method of claim 11, further comprising:
receiving information, via the GUI, indicating goals of the user related to one or more of the plurality of skin conditions;
identifying the product for use for the one of the plurality of skin conditions based on clinical treatment data of the product and the goals of the user.

14. The method of claim 11, further comprising:
identifying the beauty routine to execute for the one of the plurality of skin conditions based on a time of day of execution of the beauty routine or based on a time of year of the execution of the beauty routine.

15. The method of claim 1, further comprising:
storing, in non-transitory computer readable media, a first skincare analysis record including information for the computer graphics and the score per each of the plurality of zones of the face of the user and for each of the plurality of skin conditions of the face of the user mapped to the one of the plurality of severity levels, wherein the first skincare analysis record is associated with a first date;
generating a second skincare analysis record associated with a second date; and
based on the first date being within a threshold number of days of the second date, combining the first skincare analysis record and the second skincare analysis record into an accumulated skincare analysis record.

16. The method of claim 1, further comprising:
storing, in non-transitory computer readable media, a first skincare analysis record including information for the computer graphics and the score per each of the plurality of zones of the face of the user and for each of the plurality of skin conditions of the face of the user mapped to the one of the plurality of severity levels, wherein the first skincare analysis record is associated with a first date;
generating a second skincare analysis record associated with a second date; and
comparing the first skincare analysis record with the second skincare analysis record to identify a trend for each of the plurality of skin conditions of the face of the user.

17. A system for analyzing skin of a user, comprising:
a computing device comprising one or more processors and non-transitory computer-readable media having stored therein executable instructions, which when executed by the one or more processors, causes the computing device to perform functions comprising:
requesting, via a graphical user interface (GUI), visual media including a face of the user;
processing the visual media to generate information for each of a plurality of skin conditions of the face of the user, wherein the information comprises a score per each of a plurality of zones of the face of the user per each of the plurality of skin conditions of the face of the user, wherein the plurality of skin conditions comprise a region condition associated to a continuous region of the face and an individual condition associated with a discrete location of the face;
mapping the score per each of the plurality of zones of the face of the user and for each of the plurality of skin conditions of the face of the user to one of a plurality of severity levels associated with the plurality of skin conditions by:
computing first descriptors for the region condition, wherein the first descriptors include characteristics of color per pixel in the visual media;
computing second descriptors for the individual condition, wherein the second descriptors include characteristics of geometry for accumulated pixels of similar color;
applying a weight to each of the first descriptors and the second descriptors that is varied based on one of the plurality of skin conditions being analyzed;
identifying clusters of the first descriptors and clusters of the second descriptors with applied weights between a first threshold and a second threshold, wherein the one of the plurality of severity levels is one of a discrete number of severity levels and wherein a range of thresholds is associated with one of the discrete number of severity levels; and
associating each of the clusters with a corresponding zone and a corresponding severity level; and
for each of the plurality of skin conditions, the GUI overlaying computer graphics at locations onto the visual media including the face of the user corresponding to each zone of the plurality of zones of the face of the user, wherein the computer graphics are depicted with a color associated with the one of the plurality of severity levels for the skin condition at each of the locations of the face of the user.

18. The system of claim 17, wherein processing the visual media, comprises:
sending, via a network, the visual media to a server configured to perform computer vision processing; and receiving, from the server via the network, the information for each of the plurality of skin conditions of the face of the user.

19. A non-transitory computer-readable media having stored therein executable instructions, which when executed by a computing device having one or more processors causes the computing device to perform functions comprising:

requesting, via a graphical user interface (GUI), visual media including a face of the user;

processing the visual media to generate information for each of a plurality of skin conditions of the face of the user, wherein the information comprises a score per each of a plurality of zones of the face of the user per each of the plurality of skin conditions of the face of the user, wherein the plurality of skin conditions comprise a region condition associated to a continuous region of the face and an individual condition associated with a discrete location of the face;

mapping the score per each of the plurality of zones of the face of the user and for each of the plurality of skin conditions of the face of the user to one of a plurality of severity levels associated with the plurality of skin conditions by:

computing first descriptors for the region condition, wherein the first descriptors include characteristics of color per pixel in the visual media;

computing second descriptors for the individual condition, wherein the second descriptors include characteristics of geometry for accumulated pixels of similar color;

applying a weight to each of the first descriptors and the second descriptors that is varied based on one of the plurality of skin conditions being analyzed;

identifying clusters of the first descriptors and clusters of the second descriptors with applied weights between a first threshold and a second threshold, wherein the one of the plurality of severity levels is one of a discrete number of severity levels and wherein a range of thresholds is associated with one of the discrete number of severity levels; and associating each of the clusters with a corresponding zone and a corresponding severity level; and for each of the plurality of skin conditions, the GUI overlaying computer graphics at locations onto the visual media including the face of the user corresponding to each zone of the plurality of zones of the face of the user, wherein the computer graphics are depicted with a color associated with the one of the plurality of severity levels for the skin condition at each of the locations of the face of the user.

20. The non-transitory computer readable media of claim 19, where the functions further comprise:

based on the one of the plurality of severity levels associated with the plurality of skin conditions, the GUI displaying information related to one or more of a product for use for the plurality of skin conditions, a beauty routine to execute for the condition, and a service to schedule for the condition.

\* \* \* \* \*